US006455573B1

(12) United States Patent
Pinto et al.

(10) Patent No.: US 6,455,573 B1
(45) Date of Patent: Sep. 24, 2002

(54) GLYCOSIDASE INHIBITORS AND METHODS OF SYNTHESIZING SAME

(75) Inventors: B. Mario Pinto, Coquitlam; Blair D. Johnston, Vancouver; Ahmad Ghavami, Coquitlam, all of (CA)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 09/627,434

(22) Filed: Jul. 28, 2000

Related U.S. Application Data

(60) Provisional application No. 60/174,837, filed on Jan. 7, 2000.

(51) Int. Cl.[7] ...................... A61K 31/381; A61K 31/40; C07D 333/46; C07D 335/00; C07D 207/12
(52) U.S. Cl. ...................... 514/425; 514/183; 514/445; 514/432; 514/315; 514/517; 514/706; 548/556; 549/28; 549/66; 546/242; 558/33; 562/899; 540/1
(58) Field of Search .................. 548/556; 514/425, 514/445, 517, 706, 432, 315, 183; 549/66, 28; 558/33; 562/899; 546/242; 540/1

(56) References Cited

U.S. PATENT DOCUMENTS 6,143,932 A  * 11/2000 Dorner ...................... 564/153

OTHER PUBLICATIONS

Yuasa H et al. Tetrahedron Lett 2000, 41(34), pp. 6615–6618.*
Yuasa, H. et al., "Synthesis of Salacinol", Tetrahedron Lett. (2000), 41(34), 6615–6618, XP002168783.
Yoshikawa, Masayuki et al., "Salacinol, potent antidiabetic principle with unique thiosugar sulfonium sulfate structure from the ayurvedic traditional medicine Salacia reticulata in Sri Lanka and India", Tetrahedron Lett. (1997), 38(48), 8367–8370, XP002168784.
Database Chemabs 'Online!, Chemical Abstracts Service, Columbus, Ohio, US; Matsuda, Hisashi et al., "Antidiabetic principles of natural medicines. IV. Aldose Reductase and alpha–glucosidase inhibitors from the roots of Salacia oblonga Wall (Celastraceae) structure of a new friedelane–type triterpene, kotalageni 16–Acetate". Database accession No. 132:163473 XP002168785.
Database Chemabs 'Online!, Chemical Abstracts Service, Columbus, Ohio, US; Yoshikawa, Masayuki et al., "Antidiabetic constituents of Sri Lankan natural medicine Kotala himbutu (Salacia reticulata): absolute stereostructures of alpha–glucosidase inhibitors, salacinol and kotalanol, with unique thiosugar sulfonium sulfate inner salt structure". Database accession No. 131:106694 XP002168786.
Patent Abstracts of Japan vol. 1999, No. 05, May 31, 1999 & JP 11 029472 A (Abstract only).
Database Chemabs 'Online!, Chemical Abstracts Service, Columbus, Ohio, US; Yoshikawa, Masayuki et al. "Kotalanol, a potent alpha–glucosidase inhibitor with thiosugar sulfoniu sulfate structure, from antidiabetic ayurvedic medicine salacia reticulat", Database accession No. 129:300080 XP002168787.

* cited by examiner

Primary Examiner—Evelyn Mei Huang
(74) Attorney, Agent, or Firm—Oyen Wiggs Green & Mutala

(57) ABSTRACT

A method for synthesizing Salacinol, its stereoisomers, and non-naturally occurring selenium and nitrogen analogues thereof having the general formula (I):

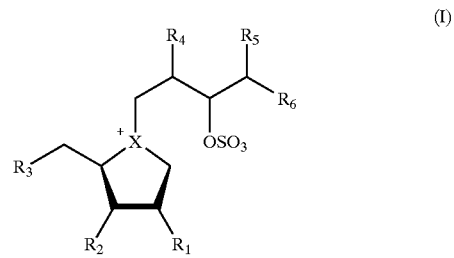

The compounds are potentially useful as glycosidase inhibitors. The synthetic schemes comprise reacting a cyclic sulfate with a 5-membered ring sugar containing a heteroatom (X). The heteroatom preferably comprises sulfur, selenium, or nitrogen. The cyclic sulfate and ring sugar reagents may be readily prepared from carbohydrate precursors, such as D-glucose, L-glucose, D-xylose and L-xylose. The target compounds are prepared by opening of the cyclic sulfates by nucleophilic attack of the heteroatoms on the 5-membered ring sugars. The resulting heterocyclic compounds have a stable, inner salt structure comprising a heteroatom cation and a sulfate anion. The synthetic schemes yield various stereoisomers of the target compounds in moderate to good yields with limited side-reactions. In an alternative embodiment of the invention, the cyclic sulfate may be similarly reacted with a 6-membered ring sugar containing a heteroatom (X) to yield a compound having the general formula (XII):

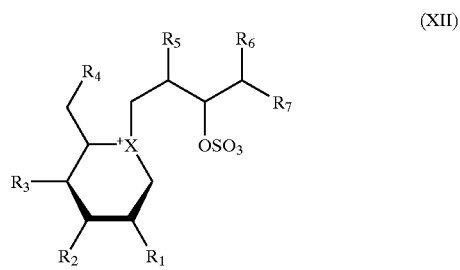

30 Claims, No Drawings

GLYCOSIDASE INHIBITORS AND METHODS OF SYNTHESIZING SAME

This application claims the benefit of U.S. provisional application No. 60/174,837, filed Jan. 7, 2000.

TECHNICAL FIELD

This application relates to methods for synthesizing Salacinol, its stereoisomers, and analogues thereof potentially useful as glycosidase inhibitors.

BACKGROUND

In treatment of non-insulin dependent diabetes (NIDD) management of blood glucose levels is critical. One strategy for treating NIDD is to delay digestion of ingested carbohydrates, thereby lowering post-prandial blood glucose concentration. This can be achieved by administering drugs which inhibit the activity of enzymes, such as glucosidases, which mediate the hydrolysis of complex starches to oligosaccharides in the small intestine. For example, carbohydrate analogues, such as acarbose, reversibly inhibit the function of pancreatic α-amylase and membrane-bound intestinal α-glucoside hydrolase enzymes. In patients suffering from Type II diabetes, such enzyme inhibition results in delayed glucose absorption into the blood and a smoothing or lowering of postprandial hyperglycemia, resulting in improved glycemic control.

Some naturally-occurring glucosidase inhibitors have been isolated from *Salacia reticulate*, a plant native to submontane forests in Sri Lanka and parts of India (known as "*Kotala himbutu*" in Singhalese). *Salacia reticulata* is a woody climbing plant which has been used in the Ayurvedic system of Indian medicine in the treatment of diabetes. Traditionally, Ayurvedic medicine advised that a person suffering from diabetes should drink water left overnight in a mug carved from Kotala himbutu wood. In an article published in 1997, Yoshikawa et al. reported the isolation of the compound Salacinol from a water-soluble fraction derived from the dried roots and stems of *Salacia reticulate*.[1] Yoshikawa et al. determined the structure of Salacinol, shown below, and demonstrated its efficacy as an α-glucosidase inhibitor.

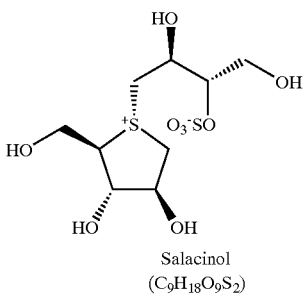

Salacinol
($C_9H_{18}O_9S_2$)

Yoshikawa et al. later reported the isolation from the roots and stems of *Salacia reticulate* of Kotalanol which was also shown to be effective as an α-glucosidase inhibitor.[2] Like Salicinol, Kotalanol contains a thiosugar sulfonium ion and an internal sulfate providing the counterion:

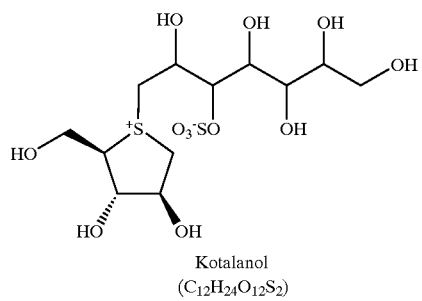

Kotalanol
($C_{12}H_{24}O_{12}S_2$)

Kotalanol has been found to show more potent inhibitory activity against sucrase than Salicinol and acarbose.[2]

The exact mechanism of action of Salacinol and other glucosidase inhibitors has not yet been elucidated. Some known glycosidase inhibitors, such as the indolizidine alkaloids castanospermine and swainsonine, are known to carry a positive charge at physiological pH.

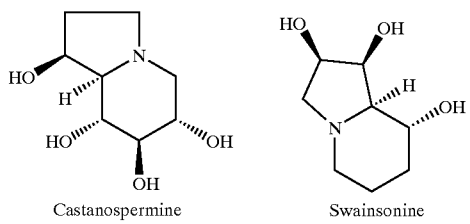

Castanospermine          Swainsonine

It is believed that the mechanism of action of some known inhibitors may be at least partially explained by the establishment of stabilizing electrostatic interactions between the inhibitor and the enzyme active site carboxylate residues. It is postulated that the compounds of the present invention, which comprise postively charged sulfonium, ammonium, and selenonium ions, could function in a similar manner. It is also possible that Salacinol and other compounds of the same class may act by alteration of a transport mechanism across the intestinal wall rather than by directly binding to glucosidase enzymes.

Salacinol and Kotalanol may potentially have fewer long-term side effects than other existing oral antidiabetic agents. For example, oral administration of acarbose in the treatment of Type II diabetes results in undesirable gastrointestinal side effects in some patients, most notably increased flatulence, diarrhoea and abdominal pain. As mentioned above, Salacinol has been used as a therapy for diabetes in the Ayurvedic system of traditional medicine for many years with no notable side effects reported. Further, recent animal studies have shown that the oral ingestion of an extractive from a *Salacia reticulate* trunk at a dose of 5,000 mg/kg had no serious acute toxicity or mutagenicity in rats.[3]

The *Salacia reticulate* plant is, however, in relatively small supply and is not readily available outside of Sri Lanka and India. Accordingly, it would be desirable if Salicinol, Kotalanol and analogues thereof could be produced synthetically.

Carbohydrate processing inhibitors have also been shown to be effective in the treatment of some non-diabetic disorders, such as cancer. While normal cells display characteristic oligosaccharide structures, tumor cells display very complex structures that are usually found in embryonic tissues. It is believed that these complex structures provide signal stimuli for rapid proliferation and metastasis of tumor cells. A possible strategy for therapeutic use of glucosidase inhibitors is to take advantage of the differential rates of normal vs cancer cell growth to inhibit assembly of complex oligosaccharide structures. For example, the indolizidine alkaloid swainsonine, an inhibitor of Golgi α-mannosidase II reportedly reduces tumor cell metastasis, enhances cellular immune responses, and reduces tumor cell growth in mice.[4] Swainsonine treatment has led to significant reduction of tumor mass in human patients with advanced malignancies, and is a promising drug therapy for patients suffering from breast, liver, lung and other malignancies.[5,6]

The compounds of the present invention may also find application in the treatment of Alzheimer's disease due to their stable, internal salt structure. Alzheimer's is characterized by plaque formation in the brain caused by aggregation of a peptide, β-amyloid, into fibrils. This is toxic to neuronal cells. One can inhibit this aggregation by using detergent-like molecules. It is believed that the compounds of the present invention, which are amphipathic, may demonstrate this activity.

The need has therefore arisen for a new class of glycosidase inhibitors which may be synthesized in high yields from readily available starting materials and which have potential use as therapeutics.

SUMMARY OF THE INVENTION

In accordance with the invention, a compound selected from the group consisting of non-naturally occurring compounds represented by the general formula (I), including stereoisomers and pharmaceutically acceptable salts thereof is disclosed,

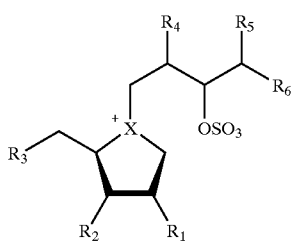
(I)

where X is selected from the group consisting of S, Se, and NH. Such compounds include stereoisomers of Salicinol. The target compounds have a stable, internal salt structure comprising heteroatom cation X and a sulfate anion; the substituents may vary without departing from the invention. Preferably, $R_1$, $R_2$, $R_3$, $R_4$ and $R_5$ are the same or different and are selected from the group consisting of H, OH, SH, $NH_2$, halogens and constituents of compounds selected from the group consisting of cyclopropanes, epoxides, aziridines and episulfides; and $R_6$ is selected from the group consisting of H and optionally substituted straight chain, branched, or cyclic, saturated or unsaturated hydrocarbon radicals, such as alkyl, alkenyl, alkynyl, aryl, and alkoxy substituents containing any suitable functionality.

Processes for the production of compounds of the general formula (I) are also disclosed comprising reacting a cyclic sulfate having the general formula (II) with a 5-membered ring sugar having the general formula

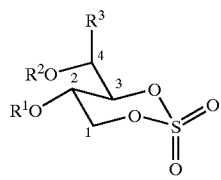
(II)

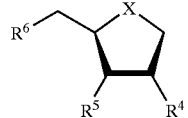
(III)

where X is selected from the group consisting of S, Se, and NH; $R^1$ and $R^2$ are selected from the group consisting of H and a protecting group; $R^3$ is selected from the group consisting of H and optionally substituted straight chain, branched, or cyclic, saturated or unsaturated hydrocarbon radicals and their protected derivatives; and $R^4$, $R^5$ and $R^6$ are the same or different and are selected from the group consisting of H, OH, SH, $NH_2$, halogens and constituents of compounds selected from the group consisting of cyclopropanes, epoxides, aziridines and episulfides and their protected derivatives. Preferably the cyclic sulfate is a 2,4-di-O-protected-D-or L-erythritol-1,3-cyclic sulfate, such as 2,4-O-Benzylidene-D-or L-erythritol-1,3-cyclic sulfate (i.e. $R^1$ and $R^2$ comprise a benzylidene protecting group); $R^3$ is H or a protected polyhydroxylated alkyl chain; and $R^4$, $R^5$ and $R^6$ are selected from the group consisting of OH and a protected OH group, such as $OCH_2C_6H_5$. The synthetic processes comprise the step of opening the cyclic sulfate (II) by nucleophilic attack of the heteroatom X on the sugar (III).

In an alternative embodiment of the invention, the cyclic sulfate (II) may be reacted with a 6-membered ring sugar having the general formula (XI) to yield a compound having the general formula (XII):

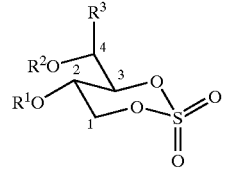
(II)

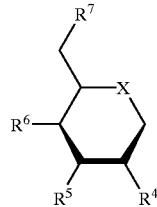
(XI)

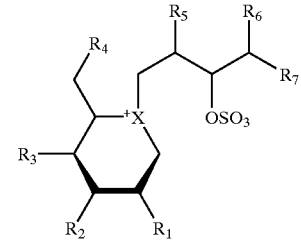
(XII)

where X is selected from the group consisting of S, Se and NH. In this embodiment $R_1$, $R_2$, $R_3$, $R_4$, $R_5$ and $R_6$ are the same or different and are selected from the group consisting of H, OH, SH, $NH_2$, halogens and constituents of compounds selected from the group consisting of cyclopropanes, epoxides, aziridines and episulfides and $R_7$ is selected from the group consisting of H and optionally substituted straight chain, branched, or cyclic, saturated or unsaturated hydrocarbon radicals. Preferably $R^1$, $R^2$ and $R^3$ are as described above in respect of compound (II) and $R^4$, $R^5$, $R^6$ and $R^7$ are selected from the group consisting of H, OH, SH, $NH_2$, halogens and constituents of compounds selected from the group consisting of cyclopropanes, epoxides, aziridines and episulfides and their protected derivatives.

The application also relates to pharmaceutical compositions comprising an effective amount of a compound according to formula (I) or (XII) together with a pharmaceutically acceptable carrier and to methods of treating carbohydrate metabolic disorders, such as non-insulin dependent diabetes, or different forms of cancer or Alzheimer's disease by administering to a subject in need of such treatment an effective amount of such compounds.

DETAILED DESCRIPTION OF THE PREFERRED EMBODIMENTS

Salacinol is a naturally occurring compound which may be extracted from the roots and stems of *Salacia reticulata*, a plant native to Sri Lanka and India. This application relates to synthetic routes for preparing Salacinol (1), and its nitrogen (2) and selenium (3) analogues shown below.

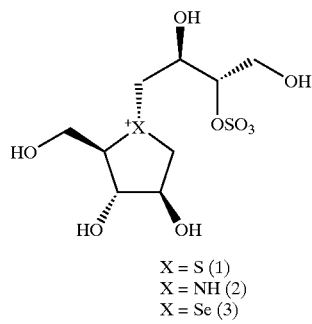

X = S (1)
X = NH (2)
X = Se (3)

This application also relates to synthetic routes for preparing the stereoisomers of compounds (1) to (3). Such analogues and stereoisomers (including stereoisomers of Salacinol) comprise a new class of compounds which are not naturally occurring and may find use as glycosidase inhibitors.

1.0 Summary of General Synthetic Scheme

Scheme 1(a) below, shows the general synthetic scheme developed by the inventors for arriving at the target compounds. To synthesize different stereoisomers of Salacinol and its nitrogen and selenium analogues (A)–(C), 5-membered-ring sugars are reacted with sulfate-containing compounds in accordance with the invention (in Scheme 1(a) the letters (A), (B), and (C) represent all stereoisomers of Salacinol and its nitrogen and selenium analogues (1), (2) and (3) respectively). The inventors followed a disconnection approach for determining the preferred synthetic route. A reasonable disconnection is one that gives the 5-membered-ring sugars (D) since they can be synthesized easily from readily available carbohydrate precursors. Nucleophilic substitution at $C_1$ of the sulfate fragment (E) can then yield the target molecules (Scheme 1(a)). A potential problem with this approach is that the leaving group (L) might act later as a base to abstract the acidic hydrogens of the sulfonium salt[7] and produce unwanted products. Therefore, the cyclic sulfate (F) may be used instead of (E) to obviate the problems associated with leaving group (L). Compound (G) may similarly be used as a cyclic sulfate reagent and is a protected version of (F).

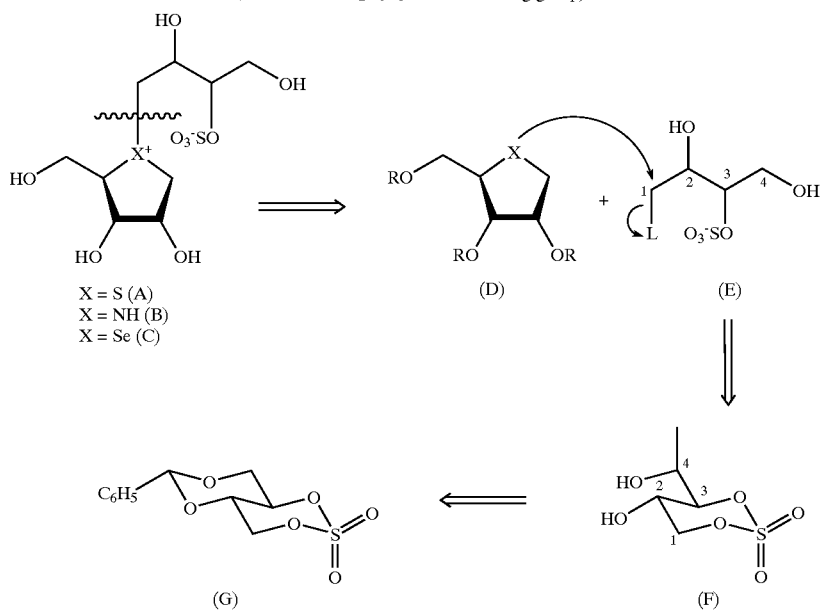

Scheme 1(a). Disconnection approach for the synthesis of (A)-(C)

(R = H, —$CH_2C_6H_5$ and L = leaving group).

Scheme 1(b) below shows generally the coupling reactions for producing the target compounds (A)–(C).

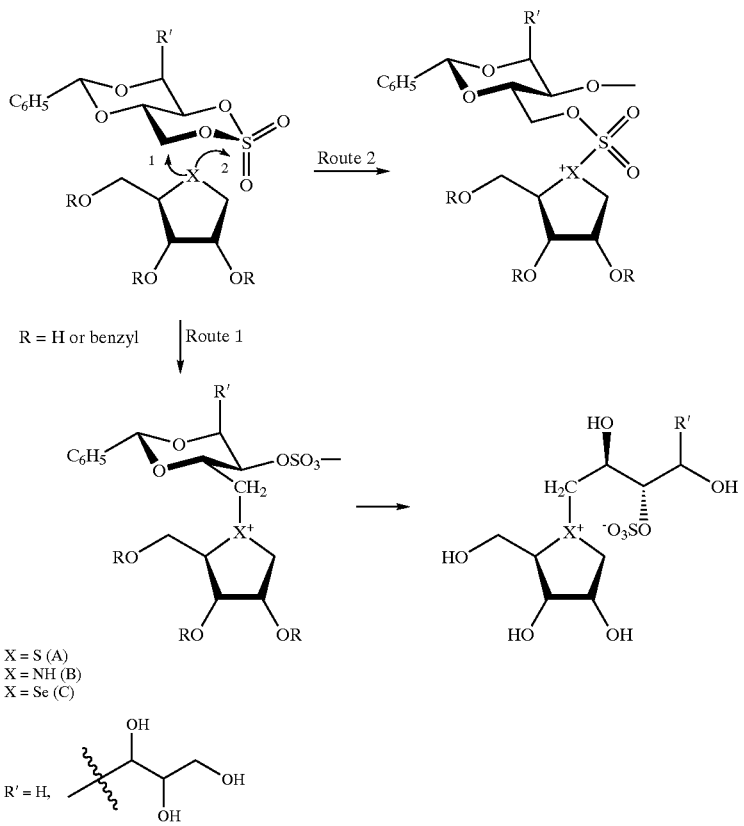

Route 1 of Scheme 1(b) shows the general strategy of reacting a cyclic sulfate with a 5-membered ring sugar to produce an intermediate compound, which may include benzyl or other protecting groups. As described in further detail below, the intermediate compound is then deprotected to yield the target compounds. The inventor s have determined that Route 2 of Scheme 1(b), a possible side reaction, does not occur.

2.0 Synthesis of Reagents

Cyclic sulfates and 5-membered-ring sugars were prepared in accordance with the synthetic schemes described below. As will be apparent to a person skilled in the art, other equivalent schemes for producing the reagents of the invention could be substituted.

2.1 Cyclic Sulfates

Cyclic sulfates were prepared in analogous fashion to the ethylidene acetal.[8] The cyclic sulfate (7) was synthesized in 4 steps starting from D-glucose (Scheme 2). 2,4-O-Benzylidene-D-erythrithol (5) was synthesized from D-glucose in two steps,[9,10] and then treated with thionyl chloride to yield the cyclic sulfite (6) which was oxidized to the cyclic sulfate (7) as described by Calvo-Flores et al.[8]

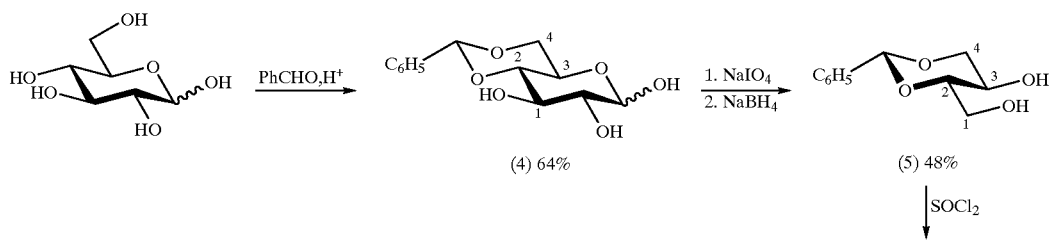

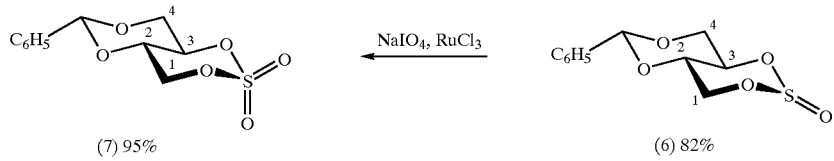

The enantiomer (10) was also synthesized using the same route but starting from L-glucose (Scheme 3).

10 was synthesized in 9 steps starting from D-glucose (Scheme 4).[11] Benzylation of the compound (11), using benzyl bro-

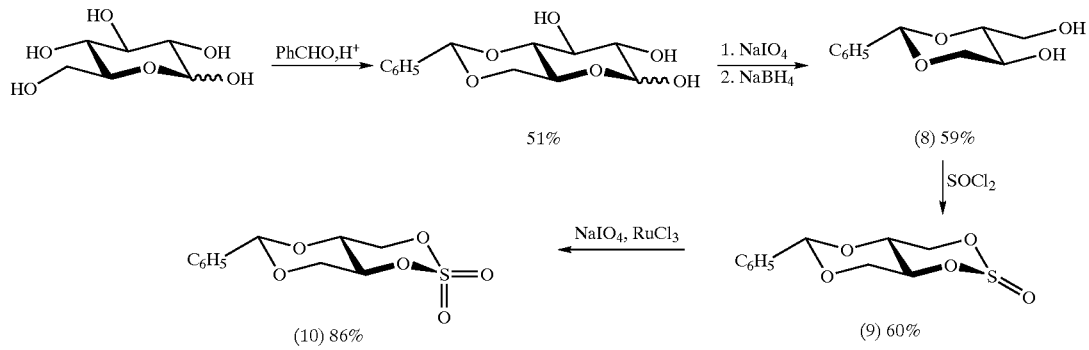

2.2 Synthesis of 5-Membered-ring Heterocycles

In order to synthesize one of the 5-membered-ring sugars (D, X=S), 1,4-anhydro-3-O-benzyl-4-thio-D-arabinitol (11), mide in DMF yielded 1,4-anhydro-2,3,5-tri-O-benzyl-4-thio-D-arabinitol (12) in 90% yield. Compound (11) was debenzylated to give 1,4-anhydro-4-thio-D-arabinitol (13) in 97% yield using a Birch reduction.

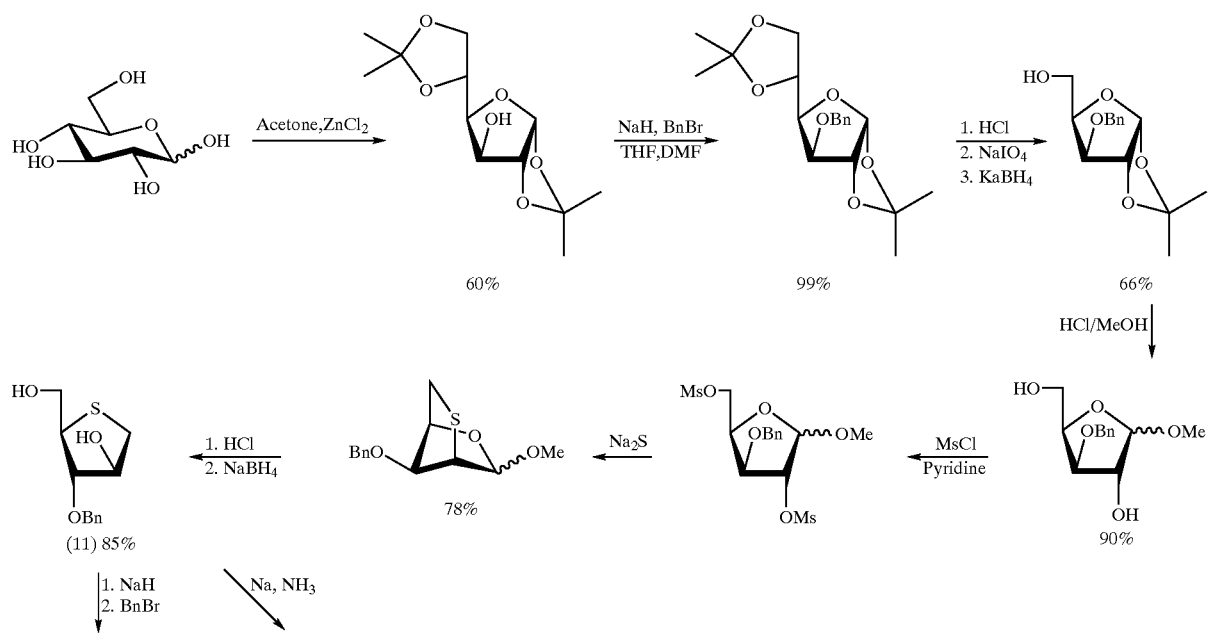

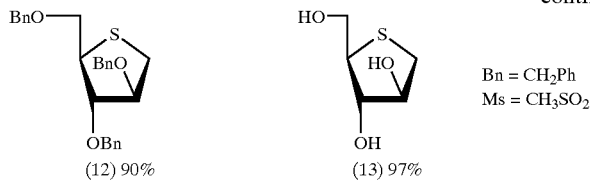

The L-isomer, 1,4-anhydro-2,3,5-tri-O-benzyl-4-thio-L-arabinitol (14) was synthesized in 5 steps starting from D-xylose (Scheme 5).[12]

sized in an analogous way starting from L-xylose (Scheme 6). Compound (19) was also synthesized in 10 steps starting from D-xylose.[13] 1,4-Anhydro-2,3,5-tri-O-benzyl-4-seleno-

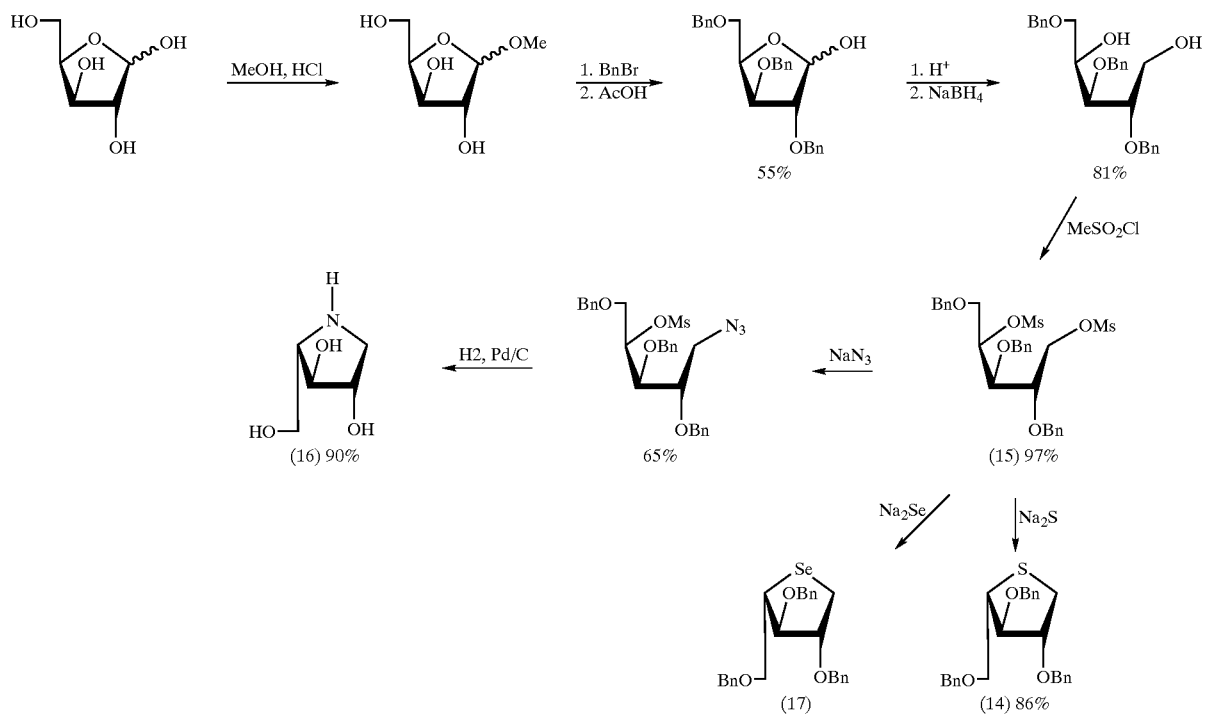

1,4-Di-O-methanesulfonyl-2,3,5-tri-O-benzyl-D-xylitol (15) is also a key intermediate for the synthesis of the aza and selena sugars (16) and (17). 1,4-Dideoxy-1,4-imino-L-arabinitol (16)[13] was synthesized in 7 steps starting from D-xylose (Scheme 5). The enantiomer (19)[13] was synthe- D-arabinitol (20) was synthesized in 5 steps starting from L-xylose (Scheme 6). To synthesize compound (20), $Na_2Se$ was made in-situ by treatment of selenium metal with sodium in liquid ammonia.

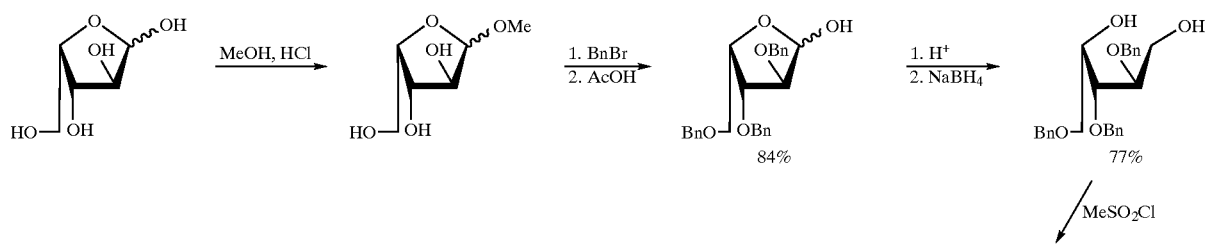

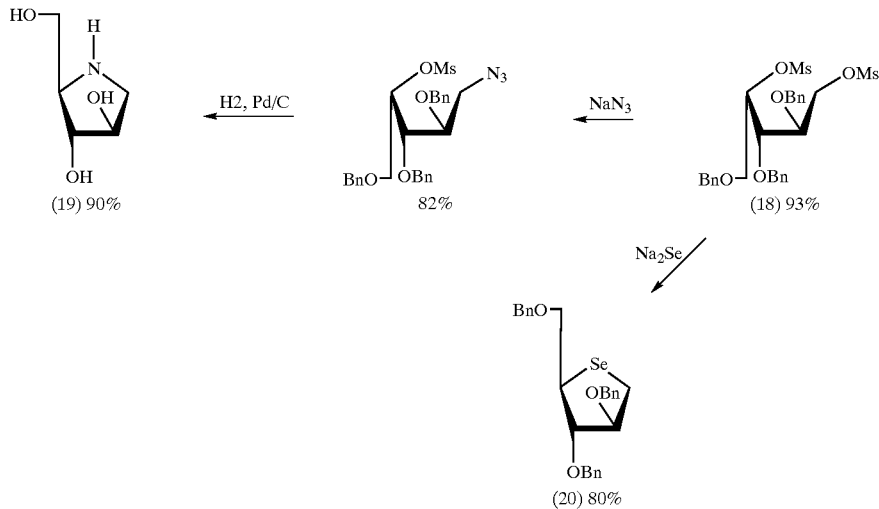

Scheme 6(a) below shows a more generalized scheme for synthesizing compound (20) using other possible protecting groups (R=COR, CH$_2$C$_6$H$_4$—OMe$_p$).

This internal salt structure may explain the stability of the target compounds toward decomposition by further nucleophilic attack.

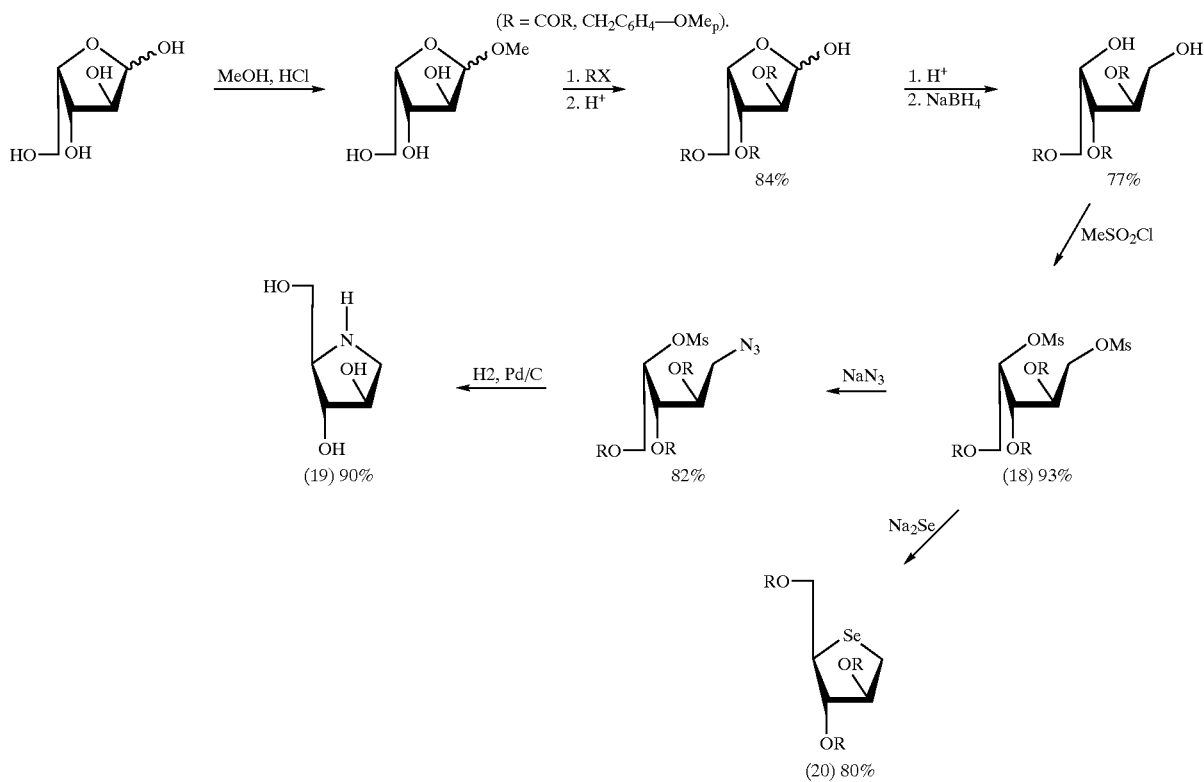

3.0 Synthesis of the Target Compounds

The target compounds (1)–(3) were prepared by opening of the cyclic sulfates by nucleophilic attack of the heteroatoms on the 5-membered rings (Scheme 1(b) above). The heteroatom gives rise to a positively charged cation and the cyclic sulfate gives rise to a negatively charged counterion.

3.1 Synthesis of Salacinol

Salacinol (1) was synthesized by nucleophilic substitution of the protected thio-arabinitol (12) with the cyclic sulfate (10) (1.2 equiv) in dry acetone containing K$_2$CO$_3$, to give the protected intermediate compound (21) in 33% yield. Hydrogenolysis of the benzyl and benzylidene groups in AcOH:H₂O, 4:1 afforded Salacinol (1) in 67% yield (Scheme 7).

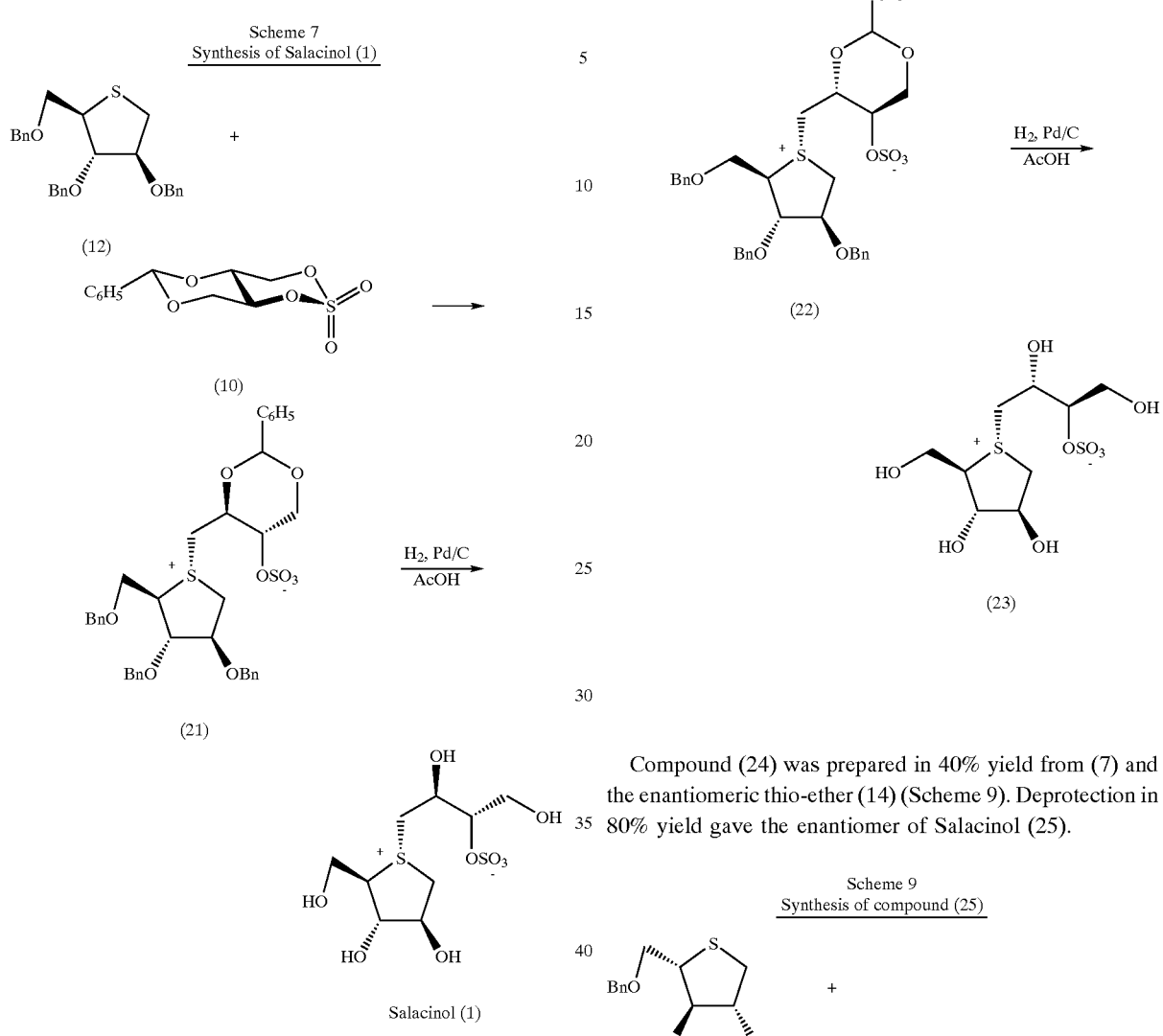

The same procedure was used to prepare intermediate compound (22) in 79% yield from the enantiomeric cyclic sulfate (7). Deprotection as before gave compound (23) in 59% yield (Scheme 8). Compound (23) is a diastereomer of Salacinol (1).

Compound (24) was prepared in 40% yield from (7) and the enantiomeric thio-ether (14) (Scheme 9). Deprotection in 80% yield gave the enantiomer of Salacinol (25).

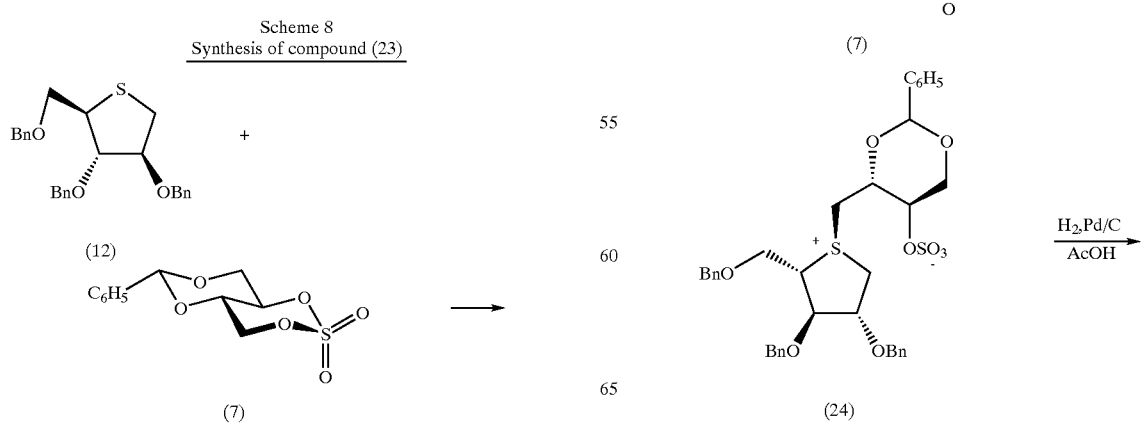

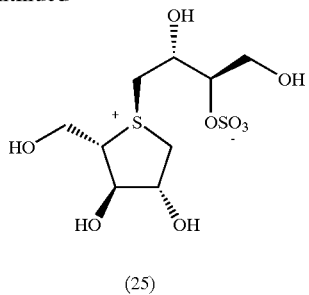

(25)

To reduce the number of synthetic steps, the inventors attempted the coupling reactions with the deprotected thio-arabinitols. Thus, the partially deprotected compound (11) was reacted with the cyclic sulfate (10) in acetone, to give compound (26) in 32% yield. Deprotection yielded Salacinol (1) in 36% yield (Scheme 10).

Scheme 10
Synthesis of Salacinol (1)

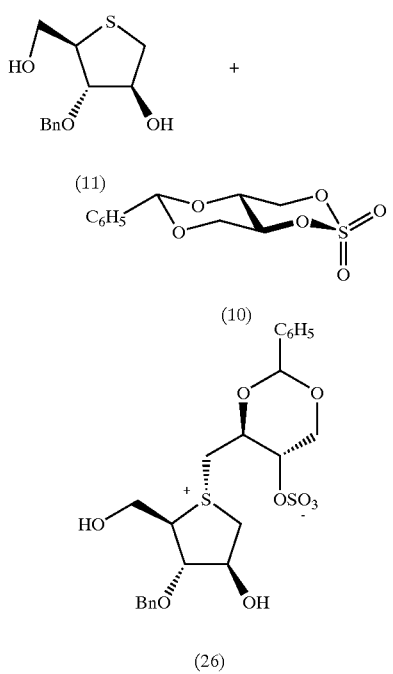

The fully-deprotected thio-arabinitol (13) was not soluble in acetone and the reaction in methanol produced several products.

3.2 Synthesis of Selenium Analogues

The seleno-analogue intermediate (27) (R=CH$_2$C$_6$H$_5$) was made starting from the seleno-arabinitol (20) (R=CH$_2$C$_6$H$_5$) and the cyclic sulfate (10) in excellent yield 86% (Scheme 11), but NMR spectroscopy showed the presence of two isomers in a ratio of 7:1 that differed in stereochemistry at the stereogenic selenium center. The isomers were separable by analytical HPLC. The inventors have assigned the name "Blintol" to the new selenium analogue (3).

Scheme 11
Synthesis of Blintol (3)

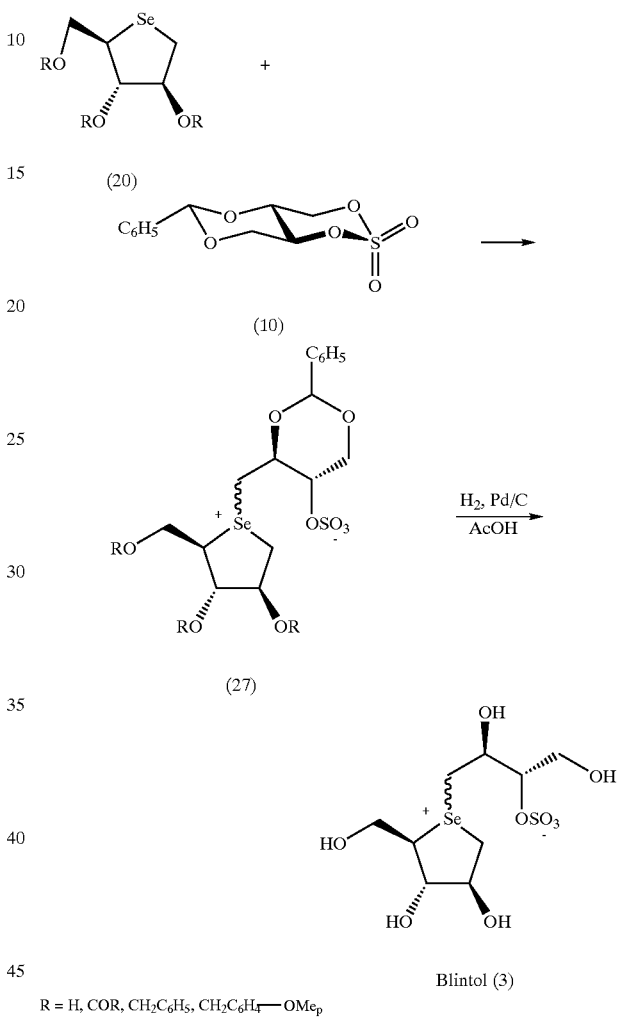

Blintol (3)

R = H, COR, CH$_2$C$_6$H$_5$, CH$_2$C$_6$H$_4$—OMe$_p$

The seleno-analogue intermediate (28) (R=CH$_2$C$_6$H$_5$) was made starting from the seleno-arabinitol (20) (R=CH$_2$C$_6$H$_5$) and the cyclic sulfate (7) in excellent yield 97% (Scheme 12); a mixture of two isomers in a ratio of 3:1 that differed in stereochemistry at the stereogenic selenium center was obtained. The isomers were separable by analytical HPLC.

Scheme 12
Synthesis of compound (29)

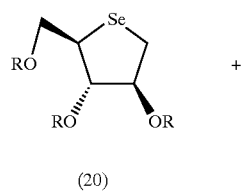

(20)

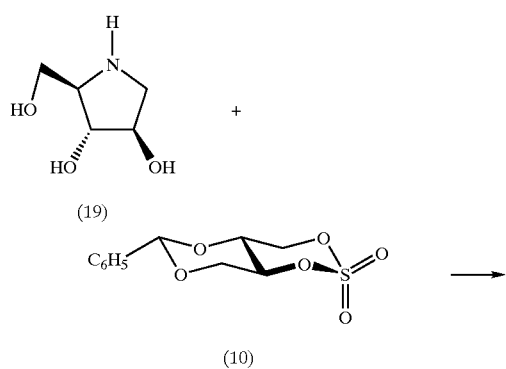

Compound (29) is a diastereomer of Blintol (3).

3.3 Synthesis of Nitrogen Analogues

The nitrogen analogue intermediate (30) was made by the reaction of the deprotected imino-arabinitol (19) with the cyclic sulfate (10) in a good yield 72% (Scheme 13). Compound (19) was not soluble in acetone so the reaction was performed in dry methanol. A side product (19%) which was identified to be the product of methanolysis of the cyclic sulfate was obtained. The inventors have assigned the name "Ghavamiol" to the new nitrogen analogue (2). Compound (30) was deprotected to give Ghavamiol (2) in 64% yield.

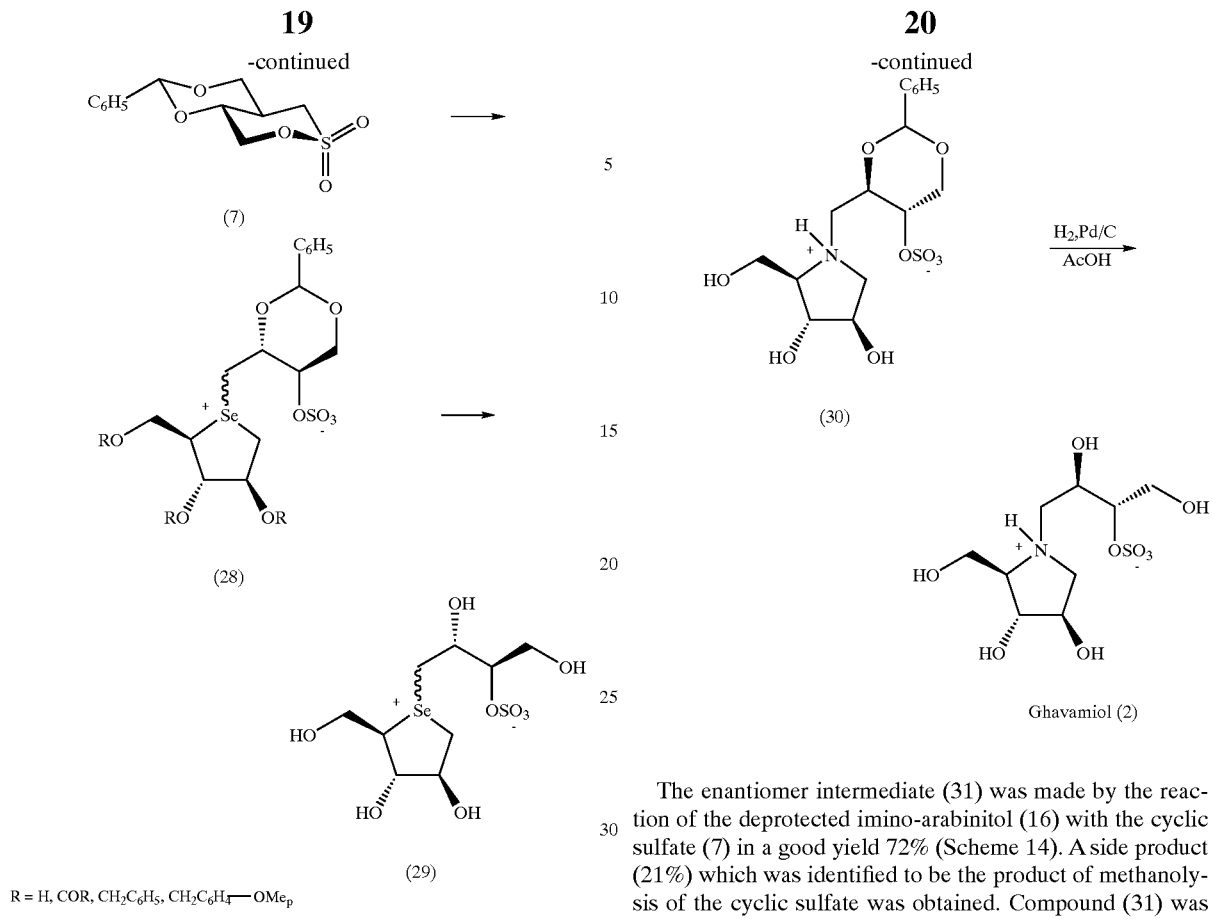

The enantiomer intermediate (31) was made by the reaction of the deprotected imino-arabinitol (16) with the cyclic sulfate (7) in a good yield 72% (Scheme 14). A side product (21%) which was identified to be the product of methanolysis of the cyclic sulfate was obtained. Compound (31) was deprotected to give compound (32) in 77% yield. Compound (32) is the enantiomer of Ghavamiol (2).

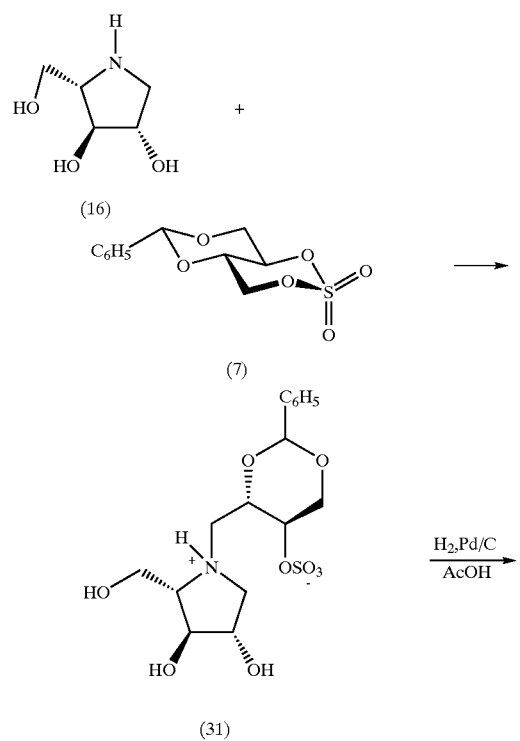

-continued

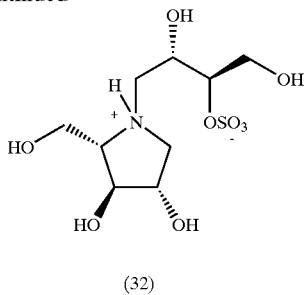

(32)

4.0 Alternative Synthetic Scheme

In an alternative embodiment of the invention, target compounds having potential application as glycosidase inhibitors may be synthesized in the manner described above using 6-membered rather than 5-membered ring heterocycles as reagents. As in the embodiments described above, the cyclic sulfate (described above) is opened in the coupling reaction due to nucleophilic attack of the heteroatoms (i.e. X=S, Se, N) on the ring sugars. As will be apparent to a person skilled in the art, the general formulas for the 6-membered sugar reagent and resulting target compound are as shown below.

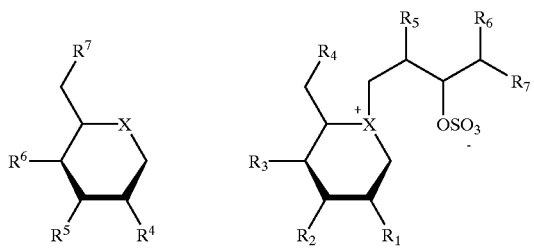

The 6-membered ring target compound shares the same internal salt structure as the 5-membered ring embodiment. The substituent groups may vary as described above without departing from the invention.

5.0 EXAMPLES

The following examples will further illustrate the invention in greater detail although it will be appreciated that the invention is not limited to the specific examples.

5.1 Experimental Methods

Optical rotations were measured at 20° C. $^1$H and $^{13}$C NMR spectra were recorded at 400.13 and 100.6 MHz for proton and carbon respectively. All assignments were confirmed with the aid of two-dimensional $^1$H,$^1$H (COSYDFTP) or $^1$H, $^{13}$C (INVBTP) experiments using standard Bruker pulse programs. MALDI-TOF mass spectra were obtained for samples dispersed in a 2,5-dihydroxybenzoic acid matrix using a Perseptive Biosystems Voyager-DE instrument. Silica gel for chromatography was Merck kieselgel 60. High resolution mass spectra were LSIMS (Fab), run on Kratos Concept H double focussing mass spectrometer at 10000 RP.

5.2 Preparation of Intermediates

5.2.1 Example 1

Preparation of Cyclic Sulfate (7) (Scheme 2)
Step 1—2,4-O-Benzylidene-D-erythritol (5)
Compound (5) was prepared from 4,6-O-benzylidene-D-glucose (4) according to standard procedures.[9,10] Compound (5) has been mentioned by MacDonald et al.,[10] without characterization, which is therefore dealt with here. Mp 138–139° C.; $[\alpha]_D$ −44° (c 1.0, MeOH); $^1$H NMR (CD$_3$OD): δ7.53–7.28 (5H, m, Ar), 5.53 (1H, s, H-5), 4.2 (1H, dd, J=10.1, 3.6 Hz, H-4a), 3.92 (1H, dd, J=12.1, 1.7 Hz, H-1a), 3.74 (1H, dd, J=12.1, 5.7 Hz, H-1b), 3.67–3.55 (3H, m, H-3, H-2, H-4b); $^{13}$C NMR (100.6 MHz, CD$_3$OD): δ139.52 ($C_{ipso}$), 129.77 ($C_{para}$), 128.99, 127.49 (4$C_{ortho+meta}$), 102.36 (C-5), 84.22 (C-3), 72.21 (C4), 62.76 (C-1), 62.59 (C-2); MALDI-TOF MS: m/e 211 (M$^+$+H), 233 (M$^+$+Na). Anal. Calcd for C$_{11}$H$_{14}$O$_4$: C, 62.83; H, 6.72. Found: C, 62.96; H, 6.55.

Step 2—2,4-O-Benzylidene-D-erythritol-1,3-cyclic sulfite (6)

A solution of the diol (5) (4.5 g, 21 mmol) and Et$_3$N (11 mL, 4 equiv) in dry CH$_2$Cl$_2$ (90 mL) was added dropwise to a solution of SOCl$_2$ (2.4 mL, 1.5 equiv) in dry CH$_2$Cl$_2$ (60 mL), with stirring in an ice-bath under an N$_2$ atmosphere. Stirring was continued at 0° C., until TLC (hex:EtOAc, 4:1) showed complete disappearance of the starting material. The mixture was diluted with CH$_2$Cl$_2$ (150 mL) and washed with H$_2$O (150 mL) and brine (150 mL). The organic solution was dried (Na$_2$SO$_4$) and concentrated on a rotary evaporator. The product was purified by flash chromatography [hex:EtOAc, 4:1+0.1% Et$_3$N] to give a mixture of two diastereomers (4.5 g, 82%). One of the isomers was selectively recrystallized from EtOAc:hex. Mp 137–139° C.; $[\alpha]_D$ +32°(c 1.0, CH$_2$Cl$_2$); $^1$H NMR (CD$_2$Cl$_2$): δ7.48–7.36 (5H, m, Ar), 5.68 (1H, s, H-5), 5.04 (1H, ddd, J=10.4, 9.5, 5.0 Hz, H-3), 4.80 (1H, dd, J=10.4, 10.4 Hz, H-1a), 4.24 (1H, dd, J=10.5, 5.0 Hz, H-4e), 4.18 (1H, ddd, J=10.4, 9.5, 4.8 Hz, H-2), 4.06 (1H, dd, J=10.4, 4.8 Hz, H-1 e), 3.89 (1H, dd, J=10.5,10.4 Hz, H-4a); $^{13}$C NMR (100.6 MHz, CD$_2$Cl$_2$): δ137.14 ($C_{ipso}$), 129.74 ($C_{para}$), 128.65, 126.50 (4$C_{ortho+meta}$), 102.72 (C-5), 73.56 (C-2), 68.16 (C-4), 63.90 (C-3), 60.18 (C-1). Anal Calcd for C$_{11}$H$_{12}$O$_5$S: C, 51.55; H, 4.72. Found: C, 51.80; H, 4.66.

Step 3—2,4-O-Benzylidene-D-erythritol-1,3-cyclic sulfate (7)

The cyclic sulfite (6) (3.5 g, 14 mmol) was dissolved in a mixture of MeCN (50 mL) and CCl$_4$ (50 mL), and NaIO$_4$ (4.1 g, 1.5 equiv) and RuCl$_3$.H$_2$O (50 mg) were added followed by H$_2$O (50 mL). The mixture was stirred vigorously at rt until TLC (hex:EtOAc,4:1) showed complete disappearance of the starting material. The mixture was diluted with Et$_2$O (200 mL) and washed with H$_2$O (200 mL) and brine (200 mL). The organic solution was dried (Na$_2$SO$_4$) and concentrated on a rotary evaporator. The product was purified by flash chromatography [hex:EtOAc, 4:1+0.1% Et$_3$N] to yield a white solid (3.5 g, 95%). A portion of the product was recrystallized from EtOAc:hex. Mp 115–125° C. (dec); $[\alpha]_D$ +4°(c 1.0, CHCl$_3$) $^1$H NMR (CD$_2$Cl$_2$): δ7.48–7.37 (5H, m, Ar), 5.65 (1H, s, H-5), 4.86 (1H, ddd, J=10.2, 9.8, 5.0 Hz, H-3), 4.76 (1H, dd, J=10.7, 10.5 Hz, H-1a), 4.65 (1H, dd, J=10.5, 5.0 Hz, H-le), 4.44 (1H, dd, J=10.5, 5.0 Hz, H4e), 4.25 (1H, ddd, J=10.7, 9.8, 5.0 Hz, H-2), 3.97 (1H, dd, J=10.5, 10.2 Hz, H4a); $^{13}$C NMR (100.6 MHz, CD$_2$Cl$_2$): δ136.32 ($C_{ipso}$) 130.03 ($C_{para}$), 128.74, 126.52 (4$C_{ortho+meta}$), 102.98 (C-5), 75.74 (C-3), 73.19(C-1), 71.68 (C-2), 67.64 (C4); MALDI-TOF MS: m/e 273 (M$^+$+ H), Anal. Calcd for C$_{11}$H$_{12}$O$_6$S: C, 48.52; H, 4.45. Found: C, 48.43; H, 4.39.

5.2.2 Example 2

Preparation of Thio-arabinitol (Scheme 4)
1,4-Anhydro-2,3,5-tri-O-benzyl-4-thio-D-arabinitol(12)
A mixture of 1,4-anhydro-3-O-benzyl-4-thio-D-arabinitol (1.0 g, 4.2 mmol) and 60% NaH (0.85 g, 5 equiv) in DMF (20 mL) was stirred in an ice-bath for 1 h. A solution of benzyl bromide (1.9 mL, 3.8 equiv) in DMF (5 mL) was added and the solution was stirred at rt for 3 h. The mixture was added to ice-water (150 mL) and extracted with Et$_2$O (150 mL). The organic solution was dried (Na$_2$SO$_4$) and concentrated. The product was purified by flash chromatography [hex:EtOAc, 4:1] to give a syrup (1.6 g, 90%). [α]$_D$ +5°(c 1.6, CHCl$_3$); $^1$H NMR (CDCl$_3$): δ7.38–7.23 (15H, m, Ar), 4.64–4.45 (6H, m, CH$_2$Ph), 4.19 (1H, dd, J=8.9, 4.6 Hz, H-2), 4.11 (1H, dd, J=7.2, 3.8 Hz, H-3), 3.69 (1H, dd, J=8.8, 7.6 Hz, H-5a), 3.57 (1H, ddd, J=7.5, 6.4, 3.6 Hz, H-4), 3.50 (1H, dd, J=8.9, 6.3 Hz, H-5b), 3.08 (1H, dd, J=11.4, 5.1 Hz, H-1a), 2.91 (1H, dd, J=11.4, 4.6 Hz, H-1b). $^{13}$C NMR (100.6 MHz, CDCl$_3$): δ138.16, 138.06, 137.88 (3C$_{ipso}$), 128.40–127.59 (15C$_{Ar}$), 85.08 (C-3), 85.04 (C-2), 73.01 (CH$_2$Ph), 72.34 (C-5), 71.85, 71.50(2CH$_2$Ph), 48.99 (C4), 33.10 (C-1). Anal. Calcd for C$_{26}$H$_{28}$O$_3$S: C, 74.25; H, 6.72. Found: C, 74.18; H, 6.53.

5.2.3 Example 3

Preparation of Seleno-arabinitol (Scheme 6)
1,4-Anhydro-2,3,5-tri-O-benzyl-4-seleno-D-arabinitol (20)

Selenium metal (1.1 g, 14 mmol) was added to liquid NH$_3$ (60 mL) in a –50° C. bath and small pieces of Na (0.71 g) were added until a blue color appeared. A small portion of selenium (20 mg) was added to remove the blue color. NH$_3$ was removed by warming on a water bath and DMF was added and removed under high vacuum to remove the rest of NH$_3$. A solution of the mesylated compound (18) (7.4 g, 12.7 mmol) in DMF (100 mL) was added and the mixture was stirred under N$_2$ in a 70° C. bath for 3 h. The mixture was cooled and the solvent was removed on high vacuum. The product was partitioned between CH$_2$Cl$_2$ (150 mL) and water (50 mL), and the organic solution was washed with water (50 mL) and brine (50 mL) and dried (MgSO$_4$). The product was purified by flash chromatography (hex:EtOAc, 3:1) to give a yellow oil (4.74 g, 80%). [α]$_D$ +22° (c 1.3, CHCl$_3$); $^1$H NMR (CDCl$_3$): δ7.22–7.48 (15H, m, Ar), 4.67, 4.61 (2H, 2d, J=11.8 Hz, CH$_2$Ph), 4.56, 4.48 (2H, 2d, J=12.1 Hz,CH$_2$Ph), 4.53, 4.50 (2H, 2d, CH$_2$Ph), 4.22 (1H, dd, J=10.1, 5.1 Hz, H-2), 4.07 (1H, dd, J=4.6, 4.6 Hz, H-3), 3.85 (1H, dd, J=9.2, 7.6 Hz, H-5a), 3.77 (1H, ddd, J=7.5, 6.9, 4.5 Hz, H-4), 3.53 (1H, dd, J=9.1, 6.8 Hz, H-5b), 3.11 (1H, dd, J=10.4, 5.1 Hz, H-1a), 2.96 (1H, dd, J=10.4, 5.3 Hz, H-1b). $^{13}$C NMR (100.6 MHz, CDCl$_3$): δ138.24, 138.21, 138.06 (3C$_{ipso}$) 128.40–127.60 (15C$_{Ar}$), 85.93 (C-2), 85.63 (C-3), 72.96 (C-5, CH$_2$Ph), 72.14, 71.50(2CH$_2$Ph), 42.59 (C-4), 23.96 (C-1). Anal. Calcd for C$_{26}$H$_{28}$O$_3$Se: C, 66.65; H, 6.03. Found: C, 66.49; H, 6.05.

5.2.4 Example 4

General Procedure for the Synthesis of the Protected Sulfonium, Selenonium and Ammonium Sulfates (21), (22), (24), (26), (27), (28), (30), (31) (Schemes 7–14)

The thio, aza or selenosugar (3 mmol) and the cyclic sulfate (1.2 equiv) were dissolved in dry acetone (in the case of (21), (22), (24), (26), (27) and (28)) or dry methanol (in the case of (30) and (31)) (0.5 mL) and anhydrous K$_2$CO$_3$ (7 mg) was added. The mixture was stirred in a Caries tube in an oil-bath (75° C.) overnight. The solvent was removed under reduced pressure and the product was purified by column chromatography.

1-((1',4'-Anhydro-2',3',5'-tri-O-benzyl-4'-thio-D-arabinitol)-4'-S-yl)-2,4-O-benzylidene-1-deoxy-L-erythritol-3-sulfate (21)

Column chromatography [CHCl$_3$:MeOH, 10:1+0.1% Et$_3$N] of the crude product gave an amorphous solid (33%). [α]$_D$ –11.9°(c 1.7, CH$_2$Cl$_2$); $^1$H NMR (CD$_2$Cl$_2$): δ7.49–7.12 (20H, m, Ar), 5.54 (1H, s, H-5), 4.59 (1H, ddd, J=9.9, 5.4, 4.5 Hz, H-3), 4.55–4.33 (8H, m, 4CH$_2$Ph, H-2', H-4a, H-1a, H-3'), 4.29 (1H, dt, J=9.5, 3.0 Hz, H-2), 4.25 and 4.15 (2H, 2d, J=11.9 Hz, CH$_2$Ph), 4.04 (1H, m, H-1'a) 4.02–3.95 (2H, m, H4', H-1b), 3.78 (1H, dd, J=10.7, 10.7 Hz, H4b), 3.74 (1H, dd, J=13.6, 3.8 Hz, H-1'b), 3.62 (1H, dd, J=9.9, 8.6 Hz, H-5'a), 3.54 (1H, dd, J=9.9, 7.2 Hz, H-5'b); $^{13}$C NMR (100.6 MHz, CD$_2$Cl$_2$): δ137.34, 137.24, 136.56, 136.39 (4C$_{ipso}$), 129.73–126.62 (20C$_{Ar}$), 101.95 (C-5), 83.75 (C-3'), 82.82 (C-2'), 76.80 (C-2), 73.73, 72.84, 72.52 (3CH$_2$Ph), 69.54. (C-4), 67.01 (C-5'), 66.48 (C-3), 65.27 (C-4'), 49.67 (C-1), 48.28 (C-1'); MALDI-TOF MS: m/e 693 (M$^+$+H). Anal. Calcd for C$_{37}$H$_{40}$O$_9$S$_2$: C, 64.14; H, 5.82. Found: C, 63.88; H, 5.83.

1-((1',4'-Anhydro-2',3',5'-tri-O-benzyl-4'-thio-D-arabinitol)-4'-S-yl)-2,4-O-enzylidene-1-deoxy-D-erythritol-3-sulfate (22)

Column chromatography [CHCl$_3$:MeOH, 10:1+01% Et$_3$N] of the crude product gave an amorphous solid (79%). [α]$_D$ –46.90 (c 0.65, CH$_2$Cl$_2$); $^1$H NMR (CD$_2$Cl$_2$): δ7.43–7.10 (20H, m, Ar), 5.49 (1H, s, H-5), 4.62–4.34 (11H, m CH$_2$Ph, H-3, H4a, H-2', H-1a, H-3'), 4.30–4.21 (2H, m, H-2, H-4'), 3.96 (1H, dd, J=9.7, 6.2 Hz, H-5'a), 3.90 (1H, dd, J=13.3, 3.4 Hz, H-1 b), 3.82 (1H, dd, J=9.8, 9.8 Hz, H-5' b), 3.79–3.71 (2H, m, H-1'a, H4b), 3.51 (1H, dd, J=13.2, 3.9 Hz, H-1' b); $^{13}$C NMR (100.6 MHz, CD$_2$Cl$_2$): δ137.62, 137.27, 136.48, 136.29 (4C$_{ipso}$), 129.80–126.56 (20C$_{Ar}$), 102.16 (C-5), 84.25 (C-3'), 82.56 (C-2'), 77.07 (C-2), 74.02, 72.74 (3CH$_2$Ph), 69.75 (C-4), 67.19 (C-5'), 66.82 (C-3), 65.76 (C-4'), 50.41 (C-1), 49.60 (C-1'); MALDI-TOF MS: m/e 693 (M$^+$+H). Anal. Calcd for C$_{37}$H$_{40}$O$_9$S$_2$: C, 64.14; H, 5.82. Found: C, 64.16; H, 5.73.

1-((1',4'-Anhydro-2',3',5'-tri-O-benzyl-4'-thio-L-arabinitol)-4'-S-yl)-2,4-O-benzylidene-1-deoxy-D-erythritol-3-sulfate (24)

Column chromatography [CHCl$_3$:MeOH, 10:1+0.1% Et$_3$N] of the crude product gave an amorphous solid (40%). [α]$_D$ +14.3°(c 1.4, CH$_2$Cl$_2$); $^1$H NMR (CD$_2$Cl$_2$): δ7.49–7.12 (20H, m,Ar), 5.55 (1H, s, H-5), 4.60 (1H, ddd J=9.8, 5.5, 4.5 Hz, H-3), 4.55–4.44 (5H, m, 3CH$_2$Ph, H-2', H4a), 4.42 (1H, dd, J=13.3, 2.3 Hz, H-1a), 4.39–4.34 (2H, m, CH$_2$Ph, H-31), 4.28 (1H, dt, J=9.8, 2.9 Hz , H-2), 4.24 and 4.14 (2H, 2d, J=11.9 Hz, CH$_2$Ph), 4.10 (1H, d, J=13.4 Hz H-1 'a), 3.98–3.90 (2H, m, H-4', H-1b), 3.78 (1H, dd, J=10.5, 10.5 Hz, H-4b), 3.67 (1H, dd, J=13.4, 3.8 Hz, H-1'b), 3.62 (1H, dd, J=9.9, 8.7 Hz, H-5'a), 3.53 (1H, dd, J=9.9, 7.2 Hz, H-5'b); $^{13}$C NMR (100.6 MHz, CD$_2$Cl$_2$): δ137.32, 137.26, 136.48, 136.25 (4C$_{ipso}$), 129.79–126.64 (20C$_{Ar}$), 102.06 (C-5), 83.96 (C-3'), 82.74 (C-2'), 76.93 (C-2), 73.81, 72.97, 72.57 (3CH$_2$Ph), 69.59.(C-4), 67.07 (C-5'), 66.36 (C-3), 66.31 (C-4'), 49.96 (C-1), 48.52 (C-1'). Anal. Calcd for C$_{37}$H$_{40}$O$_9$S$_2$: C, 64.14; H, 5.82. Found: C, 64.13; H, 5.74.

1-((1',4'-Anhydro-3'-O-benzyl-4'-thio-D-arabinitol)-4'-S-yl)-2,4-O-benzylidene-1-deoxy-L-erythritol-3-sulfate (26).

Column chromatography [CHCl$_3$:MeOH, 10:1+0.1% Et$_3$N] of the crude product gave an amorphous solid (32%).; $^1$H NMR (CD$_2$Cl$_2$): δ7.49–7.26 (10H, m, Ar), 6.22 (1H, d, J=4.4 Hz, 2'-OH), 5.54 (1H, s, H-5), 4.96 (1H, br-s, H-2'), 4.64 (1H, d, J=11.6 Hz, CH$_2$Ph), 4.64–4.62 (1H, m, 5'-OH), 4.56 (1H, d, J=11.6 Hz, CH$_2$Ph), 4.54–4.48 (1H, m, H-3), 4.46 (1H, dd, J=10.5, 5.4 Hz, H-4a), 4.33–4.25 (3H, m, H-3', H-2, H-1'a), 4.12 (1H, dd, J=13.5, 2.6 Hz, H-1a), 4.12–4.09 (1H, m, H-4'), 4.01 (1H, dd, J=13.5, 3.4 Hz, H-1b), 3.92–3.82 (2H, m, H-5'a, H-5'b), 3.78(1H, dd, J=10.5, 10.1

Hz, H-4b), 3.67(1H, dd, J=13.5, 3.9 Hz, H-1'b); $^{13}$C NMR (100.6 MHz, CD$_2$Cl$_2$): δ136.92, 136.73 (2C$_{ipso}$), 129.97–126.61(10C$_{Ar}$), 102.32 (C-5), 88.45 (C-3'), 76.61 (C-2), 76.22 (C-2'), 72.96 (CH$_2$Ph), 71.24 (C-4'), 69.27 (C-4), 66.96 (C-3), 60.51 (C-5'), 52.43 (C-1'), 48.30 (C-1); MALDI-TOF MS: m/e 513 (M$^+$+H). Anal. Calcd for C$_{23}$H$_{28}$O$_9$S$_2$: C, 53.89; H, 5.51. Found: C, 53.64; H, 5.34.

1-((1',4'-Anhydro-2',3',5'-tri-O-benzyl-4'-seleno-D-arabinitol)-4'-Se-yl)-2,4-O-benzylidene-1-deoxy-L-erythritol-3-sulfate (27)

Column chromatography [CHCl$_3$:MeOH, 15:1] of the crude product gave an amorphous solid (86%). NMR showed the presence of two isomers (7:1) at the stereogenic selenium center which were separated on analytical HPLC [acetonitrile/H$_2$O]. Anal. Calcd for C$_{37}$H$_{40}$O$_9$SSe: C, 59.99; H, 5.45. Found: C, 59.91; H, 5.44.

1-((1',4'-Anhydro-2',3',5'-tri-O-benzyl-4'-seleno-D-arabinitol)-4'-Se-yl)-2,4-O-benzylidene-1-deoxy-D-erythritol-3-sulfate (28)

Column chromatography [CHCl$_3$:MeOH, 15:1] of the crude product gave an amorphous solid (96%). NMR showed the presence of two isomers (3:1) at the stereogenic selenium center which were separated on analytical HPLC [acetonitrile/H$_2$O]. Anal. Calcd for C$_{37}$H$_{40}$O$_9$SSe: C, 59.99; H, 5.45. Found: C, 59.91; H, 5.37.

1-((1',4'-Dideoxy-1',4'-imino-D-arabinitol)-4'-N-yl)-2,4-O-benzylidene-1-deoxy-L-erythritol-3-sulfate (30)

A mixture of 1,4-Dideoxy-1,4-imino-D-arabinitol (19) (100 mg, 0.7 mmol) and 2,4-O-benzylidene-L-erythritol-1,3-cyclic sulfate (10) (235 mg, 1.2 equiv) were dissolved in dry MeOH (0.5 mL) and anhydrous K$_2$CO$_3$ (15 mg) was added. The mixture was stirred in a Caries tube in an oil-bath (75° C.) overnight. The solvent was removed under reduced pressure and column chromatography [CH$_2$Cl$_2$:MeOH, 4.5:1] of the crude product gave an amorphous solid (219 mg, 72%). $^1$H NMR (CD$_3$OD): δ7.53–7.30 (5H, m, Ar), 5.61 (1H, s, H-5), 4.53 (1H, dd, J=11.1, 5.2 Hz, H-4a), 4.25 (1H, m, H-2), 4.20 (1H, ddd, J=9.8, 5.2, 4.4 Hz, H-3), 4.11 (1H, br-s, H-2'), 3.99–3.84 (4H, m, H-1a, H-3', H-5'a, H-5'b), 3.82 (1H, dd, J=10.7, 9.8 Hz H-4b) 3.58 (1H, m, H-1'a), 3.55–3.42 (2H, m, H-1'b, H-4'), 3.38 (1H, m, H-1b); $^{13}$C NMR (100.6 MHz, CD$_3$OD): δ138.72 (C$_{ipso}$), 130.12 (C$_{para}$), 129.21, 127.39 (4C$_{ortho+meta}$), 102.33 (C-5), 78.01 (C-4', C-3', C-2), 76.31 (C-2'), 70.29 (C-4), 69.02 (C-3), 62.64 (C-1'), 60.51 (C-5'), 58.46 (C-1); MALDI-TOF MS: m/e 428 (M$^+$+Na), 406 (M$^+$+H); HRMS. Calcd for C$_{16}$H$_{23}$O$_9$SN (M+H): 406.1179. Found: 406.1192.

1-((1',4'-Dideoxy-1',4'-imino-L-arabinitol)-4'-N-yl)-2,4-O-benzylidene-1-deoxy-D-erythritol-3-sulfate (31).

A mixture of 1,4-Dideoxy-1,4-imino-L-arabinitol (16) (80 mg, 0.6 mmol) and 2,4-O-benzylidene-D-erythritol-1,3-cyclic sulfate (7) (190 mg, 1.2 equiv) were dissolved in dry MeOH (0.5 mL) and anhydrous K$_2$CO$_3$ (10 mg) was added. The mixture was stirred in a Caries tube in an oil-bath (75° C.) overnight. The solvent was removed under reduced pressure and column chromatography [CH$_2$Cl$_2$:MeOH, 5:1] of the crude product gave an amorphous solid (175 mg, 72%). $^1$H NMR (CD$_3$OD): δ7.52–7.31 (5H, m, Ar), 5.62 (1H, s, H-5), 4.53 (1H, dd, J=10.9, 5.2 Hz, H-4a), 4.28 (1H, m, H-2), 4.20 (1H, ddd, J=9.7, 5.1, 4.6 Hz, H-3), 4.14 (1H, br-s, H-2'), 4.03 (1H, m, H-1a), 3.98–3.84 (3H, m, H-3', H-5'a, H-5'b), 3.81 (1H, dd, J=10.9, 10 Hz H-4b) 3.63 (1H, m, H-1'a), 3.55–3.42 (2H, m, H-1'b, H-4'), 3.38 (1H, m, H-1b); $^{13}$C NMR (100.6 MHz, CD$_3$OD): δ138.66 (C$_{ipso}$), 130.15 (C$_{para}$), 129.23, 127.40 (4C$_{ortho+meta}$), 102.34 (C-5), 77.81 (C4'), 77.52 (C-3', C-2), 76.19 (C-2'), 70.27 (C-4), 68.92 (C-3), 62.68 (C-1'), 60.41 (C-5'), 58.61 (C-1); MALDI-TOF MS: m/e 428 (M$^+$+Na), 406 (M$^+$+H).

5.2.5 Example 5

General Procedure for the Deprotection of the Protected Sulfonium Sulfates (Schemes 7–10) and Ammonium Sulfates (Schemes 13–14)

The protected compound was dissolved in AcOH:H$_2$O, 4:1 (3 mL) and stirred with Pd—C (80 mg) under H$_2$ (52 psi). After 60 h the reaction mixture was filtered through a pad of Celite, which was consequently washed with MeOH. The combined filtrates were concentrated and the residue was purified by column chromatography.

1-((1,4'-Anhydro-4'-thio-D-arabinitol)4'-S-yl)-1-deoxy-L-erythritol-3-sulfate (1)

Column chromatography [CHCl$_3$:MeOH:H$_2$O, 7:3:1] of the crude product gave an amorphous solid (67%). [α]$_D$ +2.1° (c 0.48, MeOH); $^1$H NMR (pyridine-d5): δ5.25 (1H, ddd, J=7.4, 3.8, 3.6 Hz, H-3), 5.14–5.09 (2H, m, H-3', H-2'), 5.00 (1H, m, H-2), 4.78 (1H, dd, J=13.0, 4.9 Hz H-1a), 4.70 (1H, m, H-4'), 4.63 (1 H, dd, J=13.0, 4.0 Hz H-1b), 4.61 (1H, dd, J=11.8, 3.7 Hz H-4a)4.53 (2H, m, H-5'a, H-5'b),4.38 (1 H, dd, J=11.8, 3.8 Hz H-4b), 4.32 (2H, br-s, H-1'a, H-1'b); $^{13}$C NMR (100.6 MHz, pyridine-d5): δ79.14 (C-3), 79.06 (C-3'), 78.18 (C-2'), 72.30 (C4'), 67.44 (C-2), 62.05 (C4), 59.98 (C-5'), 52.46 (C-1), 50.35 (C-1'). HRMS. Calcd for C$_9$H$_{18}$O$_9$S$_2$ (M+H): 335.0471. Found: 335.0481.

1-((1',4'-Anhydro-4'-thio-D-arabinitol)-4'-S-yl)1-deoxy-D-erythritol-3-sulfate (23)

Column chromatography [CHCl$_3$:MeOH:H$_2$O, 7:3:1] of the crude product gave an amorphous solid (59%). [α]$_D$ −35.60 (c 0.86, MeOH); $^1$H NMR (pyridine-d5): δ5.19 (1H, ddd, J=8.0, 4.1, 3.6 Hz, H-3), 5.17–5.12 (2H, m, H-2'), H-3'), 5.00 (1H, ddd, J=8.0, 5.3, 4.1 Hz, H-2), 4.83 (1H, dd, J=13.0, 5.1 Hz H-1a), 4.78 (1 H, m, H4'), 4.65 (1 H, dd, J=11.9, 3.8 Hz H4a), 4.64–4.57 (2H, m, H-5'a, H-5'b), 4.53 (1H, dd, J=13.0, 4.1 Hz H-1b), 4.40 (1H, dd, J=11.9, 3.8 Hz H-4b), 4.29 (1H, dd, J=12.7, 3.9 Hz H-1'a), 4.17 (1H, dd, J=12.7, 2.6 Hz H-1'b); $^{13}$C NMR (100.6 MHz, pyridine-d5): δ79.46 (C-3), 79.38 (C-3'), 78.94 (C-2'), 71.94 (C4'), 67.52 (C-2), 62.02 (C4), 60.26 (C-5'), 52.64 (C-1), 51.01 (C-1'). HRMS. Calcd for C$_9$H$_{18}$O$_9$S$_2$ (M+H): 335.0471. Found: 335.0486.

1-((1',4'-Anhydro-4'-thio-L-arabinitol)-4'-S-yl)-1-deoxy-D-erythritol-3-sulfate (25)

Column chromatography [CHCl$_3$:MeOH:H$_2$O, 7:3:1] of the crude product gave an amorphous solid (80%). [α]$_D$ +1.1°(c 1.5, MeOH); $^1$H NMR (pyridine-d5): δ5.23 (1H, ddd, J=7.4, 3.8, 3.7 Hz, H-3), 5.11(1H, m, H-3'), 5.10 (1H, m, H-2'), 4.98 (1H,m, H-2), 4.76 (1H, dd, J=11.7, 3.7 Hz H-1a), 4.70 (1H, m, H-4'), 4.63 (1H, dd, J=11.7, 3.8 Hz H-1b), 4.60 (1H, dd, J=11.8, 3.7 Hz H-4a) 4.51 (2H, m, H-5'a, H-5'b), 4.35 (1 H, dd, J=11.8, 4.0 Hz H-4b), 4.31 (2H, m, H-1'a, H-1'b); $^{13}$C NMR (100.6 MHz, pyridine-d5): δ79.38 (C-3, C-2'), 78.41 (C-3'), 72.51 (C4'), 67.63 (C-2), 62.23 (C-4), 60.21 (C-5'), 52.60 (C-1), 50.57 (C-1'). HRMS. Calcd for C$_9$H$_{18}$O$_9$S$_2$ (M+H): 335.0471. Found: 335.0466.

1-((1',4'-Dideoxy-1',4'-imino-D-arabinitol)-4'-N-yl)-1-deoxy-L-erythritol-3-sulfate (2)

Column chromatography [CHCl$_3$:MeOH:H$_2$O, 7:3:1] of the crude product gave an amorphous solid (64%). $^1$H NMR (CD$_3$OD): δ4.26–4.20 (2H, m H-2, H-3), 4.15 (1H, m, H-2'), 3.98 (1H,br-s, H-3'), 3.94–3.87 (3H,m, H-5'a, H-5b', H-4a) 3.81 (1H, dd, J=12.0, 3.5 Hz H-4b), 3.74–3.62 (2H, m, H-1a, H-1'a), 3.49–3.42 (1H, m, H-1'b), 3.40–3.35 (1H, m, H-4'), 3.15 (1H, m, H-1b); $^{13}$C NMR (100.6 MHz, CD$_3$OD): δ81.17 (C-3), 78.27 (C-3'), 77.86 (C-4'), 76.19 (C-2'), 68.07 (C-2), 62.57 (C-1'), 61.67(C-4), 60.72 (C-1, C-5'). HRMS. Calcd for C$_9$H$_{18}$O$_9$SN (M+H): 318.0859. Found: 318.0863.

1-((1',4'-Dideoxy-1',4'-imino-L-arabinitol)-4'-N-yl)-1-deoxy-D-erythritol-3-sulfate (32)

Column chromatography [CHCl$_3$:MeOH:H$_2$O, 7:3:1] of the crude product gave an amorphous solid (77%). $^1$H NMR (CD$_3$OD): δ4.25 (1H, m H-2), 4.23(1H, m, H-3), 4.16 (1H, br-s, H-2'), 3.99 (1H,br-s, H-3'), 3.94–3.87 (3H,m, H-5'a, H-5b', H-4a), 3.81 (1H, dd, J=12.1, 3.6 Hz H-4b), 3.77–3.64 (2H, m, H-1a, H-1'a), 3.55–3.39 (2H, m, H-1b, H-4'), 3.22 (1H, m, H-1b): $^{13}$C NMR (100.6 MHz, CD$_3$OD): δ81.18 (C-3), 78.23 (C-3', C-4'), 76.10 (C-2'), 68.05 (C-2), 62.66 (C-1'), 61.88(C-4), 60.49 (C-1, C-5'). HRMS. Calcd for C$_9$H$_{18}$O$_9$SN (M+H): 318.0859. Found: 318.0856.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A compound selected from the group consisting of compounds represented by the formula (I) and stereoisomers and pharmaceutically acceptable salts thereof:

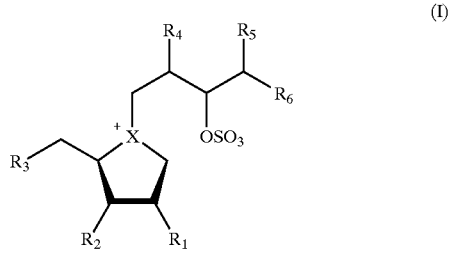

(I)

wherein X is selected from the group consisting of S, Se and NH; R$_1$, R$_2$, R$_3$, and R$_4$ are the same or different and are selected from the group consisting of H, OH, SH, NH$_2$, and halogens; R$_5$ is selected from the group consisting of H and C$_3$H$_7$O$_3$; and R$_6$ is selected from the group consisting of OH and alkyl, alkenyl, alkynyl, aryl, and alkoxy substituents, said compound excluding naturally occurring Salacinol and Kotalanol having the structures (A) and (B)

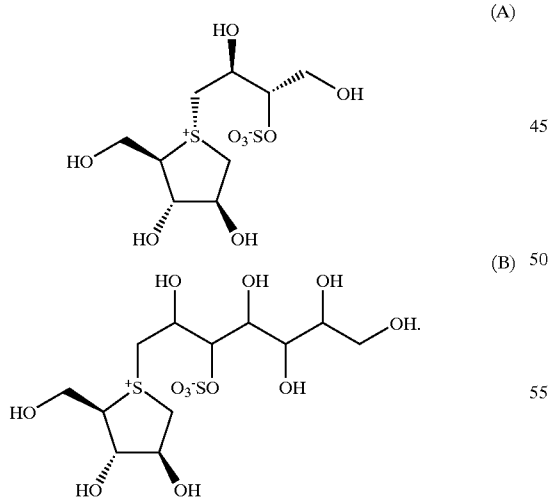

2. A pharmaceutical composition comprising an effective amount of a compound according to claim 1 together with a pharmaceutically acceptable carrier.

3. The compound as defined in claim 1, wherein R$_1$, R$_2$, R$_3$, R$_4$ and R$_6$ are OH and R$_5$ is H.

4. The compound as defined in claim 1, wherein R$_1$, R$_2$, R$_3$, R$_4$ and R$_5$ are OH and R$_6$ is C$_3$H$_7$O$_3$.

5. The process as defined in claim 1, wherein said cyclic sulfate is a 2,4-di-O-protected-D- or L-erythritol-1,3-cyclic sulfate.

6. The process as defined in claim 5, wherein said cyclic sulfate is 2,4-O-Benzylidene-D- or L-erythritol-1,3-cyclic sulfate.

7. The process as defined in claim 1, wherein R$^3$ is a protected polyhydroxylated alkyl chain.

8. The process as defined in claim 1, wherein R$^4$, R$^5$, and R$^6$ are selected from the group consisting of OH and OCH$_2$C$_6$H$_5$.

9. The process as defined in claim 1, wherein the reaction is carried out in a solvent selected from the group consisting of acetone and methanol.

10. The process as defined in claim 9, further comprising the step of adding a base to said solvent.

11. The process as defined in claim 10, wherein said base is K$_2$CO$_3$.

12. A process for the production of a compound of having the formula (I$^A$)

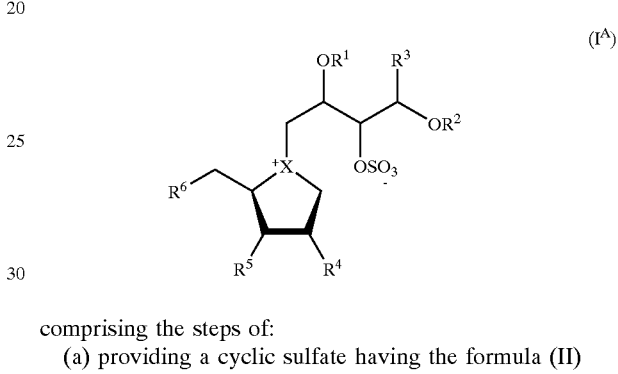

(I$^A$)

comprising the steps of:
(a) providing a cyclic sulfate having the formula (II)

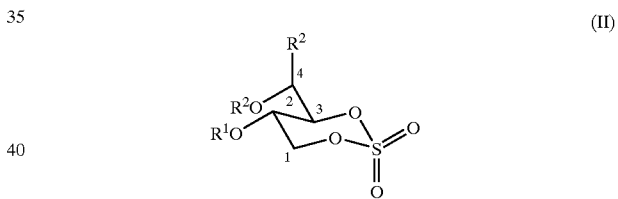

(II)

wherein R$^1$ and R$^2$ are H or a protecting group and R$^3$ is selected from the group consisting of H and alkyl, alkenyl, alkynyl, aryl, polyhydroxylated ally and alkoxy substituents and protected derivatives of polyhydroxylated alkyl substituents;

(b) providing a 5-membered sugar of the formula (III),

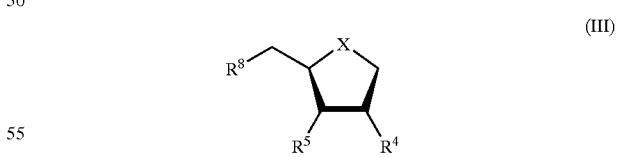

(III)

wherein X is selected from the group consisting of S, Se, and NH and R$^4$, R$^5$ and R$^6$ are OH or a protected OH group;

(c) reacting the cyclic sulfate (II) with the 5-membered sugar (III), wherein the cyclic sulfate (II) is opened by nucleophilic attack of the heteroatom X on the sugar (III) to produce an intermediate compound having an internal salt structure comprising a positively charged heteroatom X and a negatively charged sulfate counterion; and (d) removing any protecting groups from said intermediate compound.

13. The process as defined in claim 12, wherein the removal of the protecting groups is performed by hydrogenolysis of said intermediate compound.

14. A non-naturally occurring stereoisomer of Salacinol selected from the group consisting of compounds (IV) and (V)

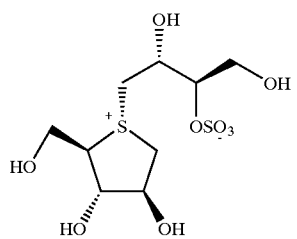
(IV)

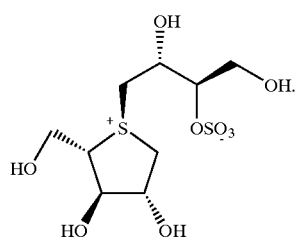
(V)

15. The process as defined in claim 12, wherein said cyclic sulfate is 2,4-O-Benzylidene-D- or L-erythritol-1,3-cyclic sulfate.

16. A process for the production of a compound having the formula (VI) comprising reacting a cyclic sulfate selected from the group consisting of compounds having the formulas (VII) and (VIII) with a sugar compound having the formula (IX) where R=H, COR, $CH_2C_6H_5$, $CH_2C_6H_4$—$OMe_p$:

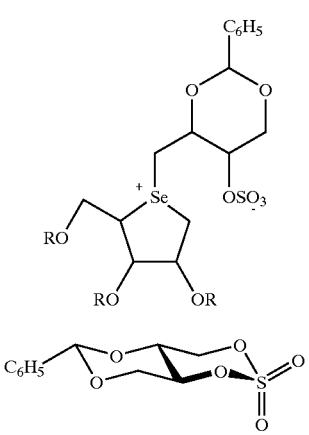
(VI)

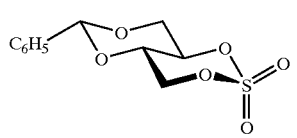
(VII)

(VIII)

-continued

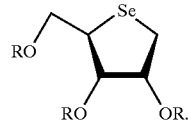
(IX)

17. A non-naturally occurring nitrogen analogue of Salacinol selected from the group consisting of compounds having the structures (2) and (32)

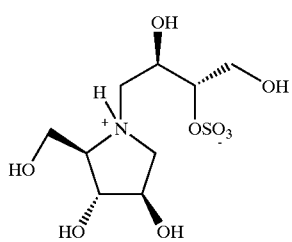
Ghavamiol (2)

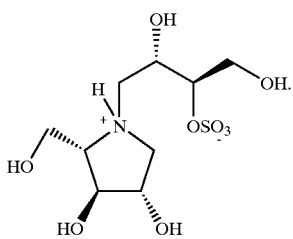
(32)

18. A pharmaceutical composition comprising an effective amount of a compound according to claim 17 together with a pharmaceutically acceptable carrier.

19. A non-naturally occurring selenium analogue of Salacinol selected from the group consisting of compounds having the structures (3) and (29)

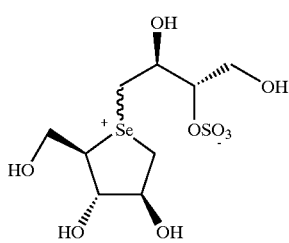
Blintol (3)

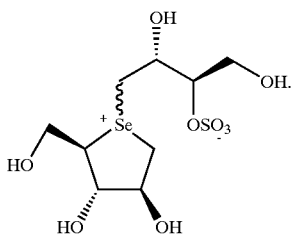
(29)

20. A pharmaceutical composition comprising an effective amount of a compound according to claim 19 together with a pharmaceutically acceptable carrier.

21. A process for the production of a compound of having the formula ($I^A$)

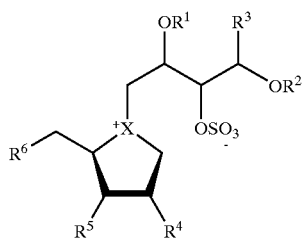

(I^A)

comprising reacting a cyclic sulfate having the general formula (II) with a 5-membered ring sugar having the formula (III)

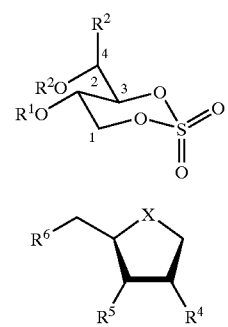

wherein the cyclic sulfate (II) is opened by nucleophilic attack of the heteroatom X on the sugar (III), where X is selected from the group consisting of S, Se, and NH; $R^1$ and $R^2$ are selected from the group consisting of H and a protecting group; $R^3$ is selected from the group consisting of H and alkyl, alkenyl, alkynyl, aryl, polyhydroxylated alkyl and alkoxy substituents; and $R^4$, $R^5$ and $R^6$ are the same or different and are selected from the group consisting of halogens, H, OH, SH, $NH_2$, and protected derivatives of OH, SH, and $NH_2$.

22. The process of claim 21 for synthesis of a compound having structure (1) comprising the steps set forth in either of Schemes 7 or 10:

Scheme 7

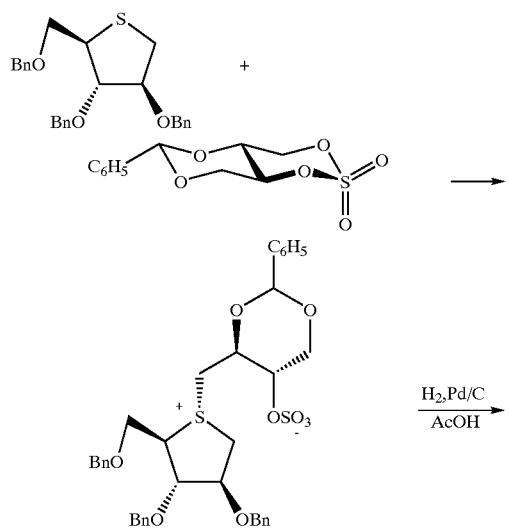

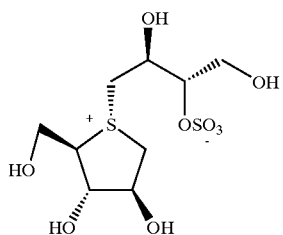

(1)

Scheme 10

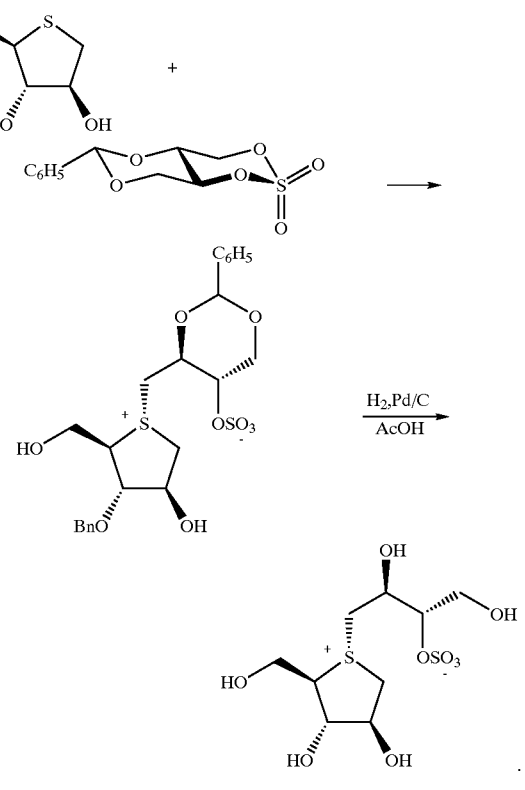

23. The process of claim 21 for synthesis of a compound having structure (23) comprising the steps set forth in Scheme 8:

Scheme 8

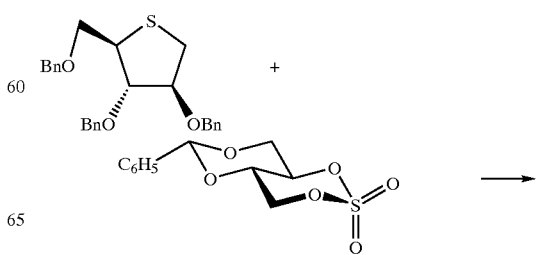

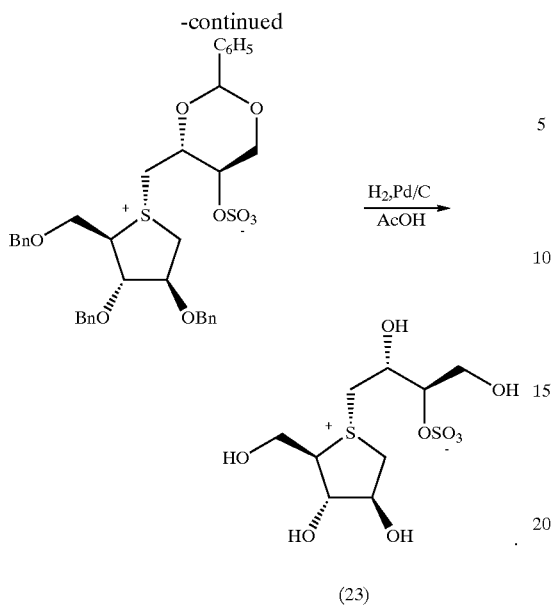
(23)
24. The process of claim 21 for synthesis of a compound having structure (25) comprising the steps set forth in Scheme 9:
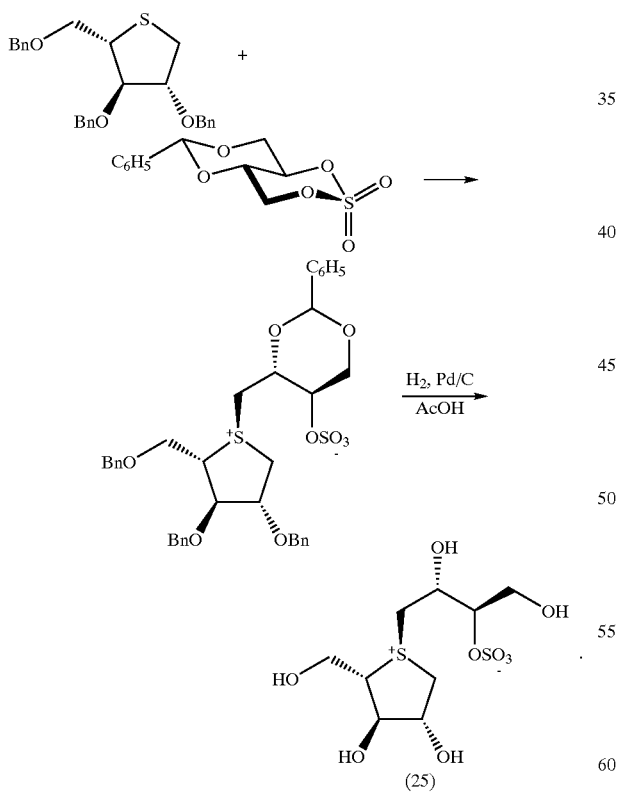
(25)
25. The process of claim 21 for synthesis of a selenium analogue of Salacinol having structure (3) or (29) comprising the steps set forth in either of Schemes 11 or 12:
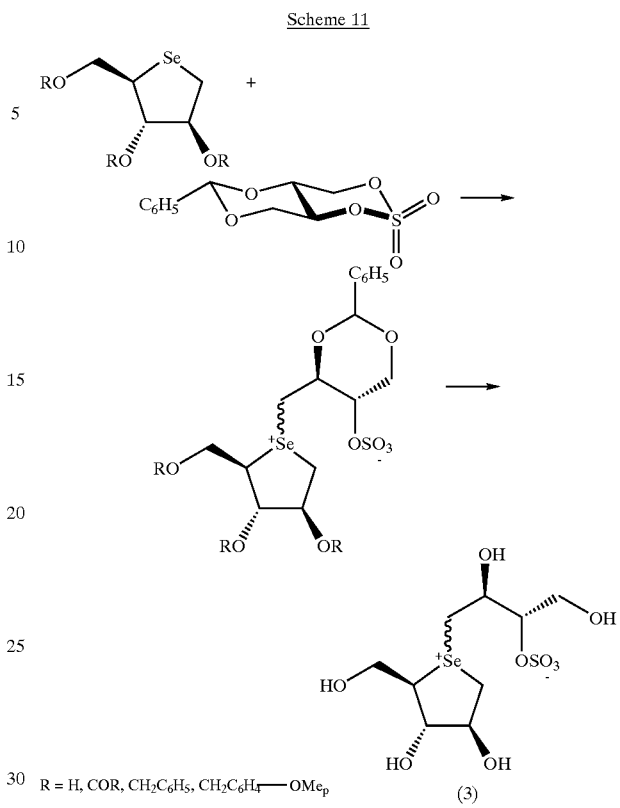
R = H, COR, CH$_2$C$_6$H$_5$, CH$_2$C$_6$H$_4$—OMe$_p$. (3)
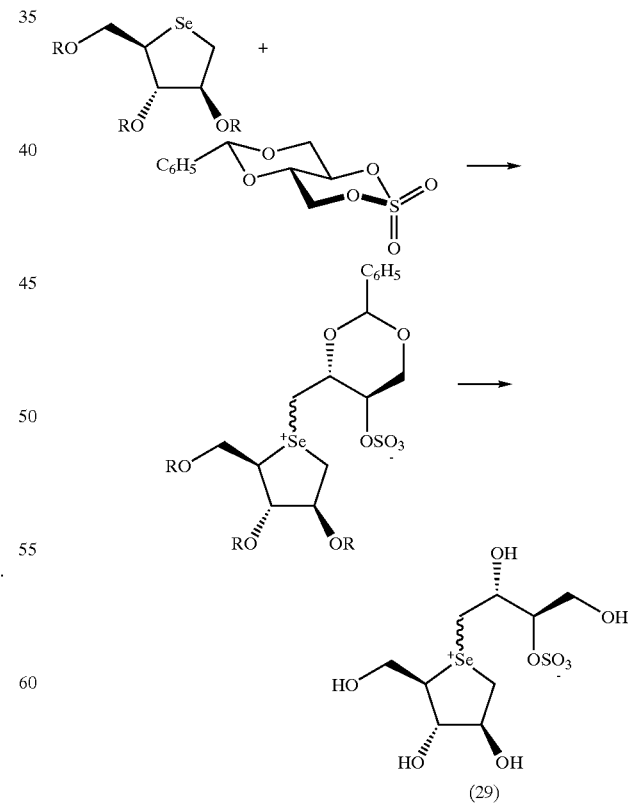
R = H, COR, CH$_2$C$_6$H$_5$, CH$_2$C$_8$H$_4$—OMe$_p$. (29)

26. The process of claim 21 for synthesis of a nitrogen analogue of Salacinol having structure (2) or (32) comprising the steps set forth in either of Schemes 13 or 14:

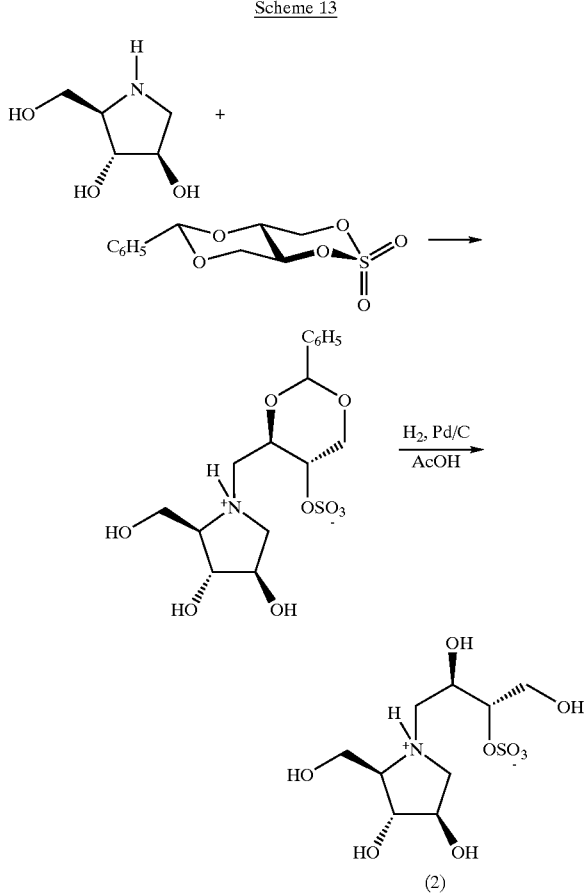

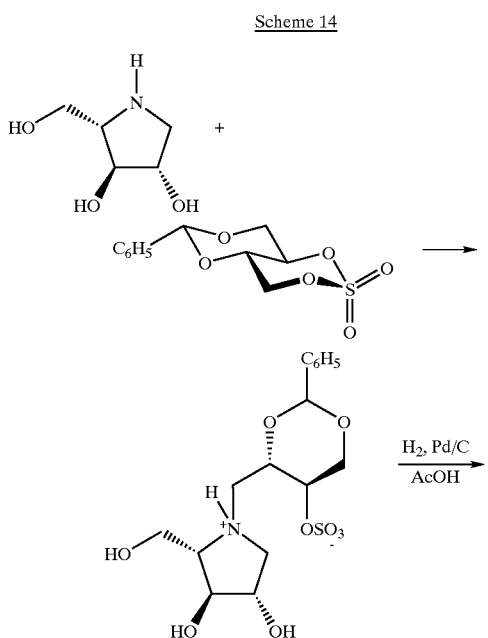

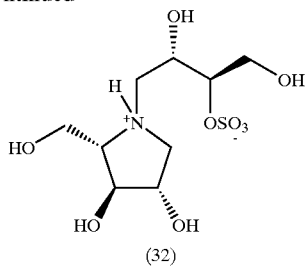

27. A compound selected from the group consisting of compounds represented by the formula (I) and stereoisomers and pharmaceutically acceptable salts thereof:

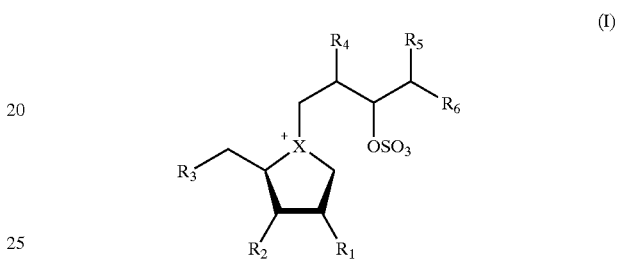

wherein X is selected from the group consisting of S, Se and NH; $R_1$, $R_2$, $R_3$ and $R_4$ are the same or different and are selected from the group consisting of halogens, H, OH, SH, $NH_2$, cyclopropanes, epoxides, aziridines and episulfides; $R_5$ is selected from the group consisting of H and $C_3H_7O_3$; and $R_5$ is selected from the group consisting of OH and alkyl, alkenyl, alkynyl, aryl, and alkoxy substituents, said compound excluding naturally occurring Salacinol and Kotalanol having the structures (A) and (B)

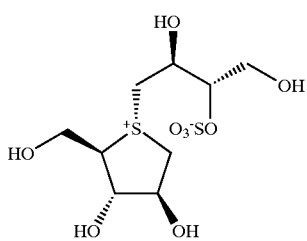

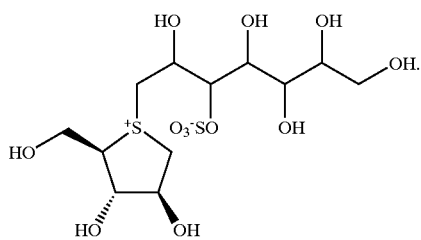

28. A method of treating diabetes in an affected patient comprising the step of administering to said patient a therapeutically effective amount of a compound according to claim 1.

29. The process of claim 12, wherein said protecting group is selected from the group consisting of benzyl and benzylidene formed by linking $R^1$ and $R^2$ together.

30. The process of claim 21, wherein said protecting group is selected from benzyl and benzylidene formed by linking $R^1$ and $R^2$ together.

* * * * *